United States Patent
Moore et al.

(10) Patent No.: US 7,115,711 B1
(45) Date of Patent: Oct. 3, 2006

(54) RETINOID X RECEPTOR-INTERACTING POLYPEPTIDES AND RELATED MOLECULES AND METHODS

(75) Inventors: David Moore, Hingham, MA (US); Wongi Seol, Cambridge, MA (US); Hueng-Sik Choi, Taejon (KR)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/365,576

(22) Filed: Aug. 2, 1999

Related U.S. Application Data

(62) Division of application No. 08/372,652, filed on Jan. 13, 1995, now Pat. No. 5,932,699.

(51) Int. Cl.
C07K 14/00 (2006.01)
(52) U.S. Cl. .................................................... 530/350
(58) Field of Classification Search .................... None
See application file for complete search history.

(56) References Cited

U.S. PATENT DOCUMENTS

| 4,981,784 A | | 1/1991 | Evans et al. | |
| 5,514,578 A | * | 5/1996 | Hogness et al. | 435/240.2 |
| 5,639,616 A | * | 6/1997 | Liao et al. | 435/7.1 |

FOREIGN PATENT DOCUMENTS

| WO | WO 88/03168 | 5/1988 |
| WO | WO 90/07517 | 1/1989 |

OTHER PUBLICATIONS

Amero et al., Mol. Endocrinol. 6:3-7, 1992.
Baes et al., Mol. Cell. Biol. 14:1544-1552, 1994.
Blumberg et al., Proc. Natl. Acad. Sci. USA 89:2321-2325, 1992.
Brent et al., Endocrinol. 3:1996-2004, 1989.
Bugge et al., EMBO J. 11:1409-1418, 1992.
Danielian et al., EMBO J. 11:1025-1033, 1992.
de The et al., Nature 343:177-180, 1990.
Evans, Science 240:889-895, 1988.
Fields et al., Nature 340:245-246, 1989.
Giguere et al., Genes & Dev. 8:538-553, 1994.
Green et al., Nature 325:75-78, 1987.
Gyuris et al., Cell 75:791-803, 1993.
Issemann et al., Nature 347:645-650, 1990.
Laudet et al., EMBO J. 11:1003-1013, 1992.
Leid et al., Trends Biochem. Sci. 17:427-433, 1992.
Leid et al., Cell 68:377-395, 1992.
Leroy et al., EMBO J. 10:59-69, 1991.
Ma et al., Cell 51:113-119, 1987.
Mangelsdorf et al., Nature 345:224-229, 1990.
Mangelsdorf et al., Cell 66:555-561, 1991.
Mangelsdorf et al., Genes & Dev. 6:329-344, 1992.
Oro et al., Nature 347:298-301, 1990.
Riddilough et al., EMBO J. 6:3729-3734, 1987.
Seagraves et al., Genes & Dev. 4:204-219, 1990.
Song et al., Proc. Natl. Acad. Sci. USA 91:10809-10813, 1994.
Yang et al., Genomics 7:509-516, 1990.
Yu et al., Cell 67: 1251-1266, 1991.
Zervos et al., Cell 72:223-232, 1993.
Zhang et al., Nature 358:587-591, 1992.
Thomas et al., Nature 362:471-475, 1993.
Bowie et al., Science 247:1307-1310, 1990.
Lee et al., Mol. Endocrinol. 8:1245-52, 1994.
Mangelsdorf et al., Cell 83:841-50, 1995.
Seol et al., Mol. Endocrinol. 9:72-85, 1995.
Darnell et al., Molecular Cell Biology, Scientific American Books, Inc., New York, p. 255, 1986.
George et al., Macromolecular Sequencing and Synthesis, Alan R. Liss, Inc., New York, pp. 127-149, 1988.
Hörlein et al., "Ligand-Independent Repression by the Thyroid Hormone Receptor Mediated by a Nuclear Receptor Co-Repressor," *Nature* 377:397-404 (1995).

* cited by examiner

*Primary Examiner*—Michael Pak
(74) *Attorney, Agent, or Firm*—Clark & Elbing LLP

(57) ABSTRACT

Disclosed is a method for determining whether a test protein is capable of interacting with a retinoid X receptor protein. The method involves: (a) providing a host cell which contains (i) a reporter gene operably linked to a protein binding site; (ii) a first fusion gene which expresses a first fusion protein, the first fusion protein including a retinoid X receptor protein covalently bonded to a binding moiety which is capable of specifically binding to the protein binding site; and (iii) a second fusion gene which expresses a second fusion protein, the second fusion protein including the test protein covalently bonded to a gene activating moiety; and (b) determining whether the test protein increases expression of the reporter gene as an indication of its ability to interact with the retinoid X receptor protein. Also disclosed is purified DNA encoding retinoid X receptor-interacting proteins and the polypeptides expressed from such DNA.

12 Claims, 19 Drawing Sheets

|  | RIP14 Clone No | | |
|---|---|---|---|
| Specific to RIP14-2 clone 3 | 3 | 12 | 6 |

```
TGGTCACCCAGGCTTCTGCTTCAGTCTCTCCTCCTTCTCCTCCTCAGCCCACTGTCTCCT  60    -    -
CATCTCACCCC                                                   71    -    -
```

Specific to RIP14-2 clone 12

```
AAAATTACTGGGCACTAGAAAGGAAGACTGGGCTCCGAATCCTCTTAGAGCCTTGGACAT  -    60   -
CTCACCCG                                                      -    68   -
```

Common to RIP14-2

```
AGAGAAGAACCGAGTTCTGAGAGTCTACAGCAAAATTACTGGGCACTAGAAAGGAAGACT 131  128   -
GGGCTCCGAATCCTCTTAGAGCCTTGGACATCTCTGGCCCAAAGCAATCCAAGGATCTTA 191  188   -
TTTGAGGACCACCATCCCAGAAGTACTTTCTCAAGGTTGAAAAGTTGGAGTGGTAGCCAA 251  248   -
GATGAATCTGATTGGGCACTCCATTTACAGGCTACGGACGAGTTTTCTCTTTCTGAAAGC 311  308   -
TTATTT                                                       317  314   -
```

Specific to RIP14-1

```
GGAAGCTAAGGATGGTGATGCAGTTTCAGGGCTTAGAAAATCCAATTCAGATTAGTCTTC  -    -   60
         M  V  M  Q  F  Q  G  L  E  N  P  I  Q  I  S  L       -    -   16

ACCACAGCCACCGGCTGTCAGGATTTGTGCCGGACGGGATGAGTGTGAAGCCAGCTAAA   -    -  119
 H  H  S  H  R  L  S  G  F  V  P  D  G  M  S  V  K  P  A  K   -    -   36
```

Common to both isoforms

```
GGTATGCTAACAGAACACGCGGCAGGCCCTCTGGGGCAGAATCTGGATTTGGAATCGTACT 378  375  180
 G  M  L  T  E  H  A  A  G  P  L  G  Q  N  L  D  L  E  S  Y    19   19   56

CCCCATACAACAATGTCCCGTTTCCTCAAGTTCAGCCACAGATTTCCTCCTCGTCTTACT  438  435  240
 S  P  Y  N  N  V  P  F  P  Q  V  Q  P  Q  I  S  S  S  S  Y    39   39   76

ATTCCAACCTGGGCTTCTACCCCCAACAACCGGAAGACTGGTATTCTCCTGGCATCTATG  498  495  300
 Y  S  N  L  G  F  Y  P  Q  Q  P  E  D  W  Y  S  P  G  I  Y    59   59   96

AACTCAGGCGAATGCCCGCTGAGACTGGGTACCAGGGAGAGACTGAGGTATCAGAGATGC  558  555  360
 E  L  R  R  M  P  A  E  T  G  Y  Q  G  E  T  E  V  S  E  M    79   79  116

CTGTGACAAAGAAGCCGCGAATGGCCGCGGCATCGGCAGGCAGAATAAAAGGGGATGAGC  618  615  420
 P  V  T  K  K  P  R  M  A  A  A  S  A  G  R  I  K  G  D  E    99   99  136

TGTGTGTTGTCTGTGGAGACAGGGCCTCTGGGTACCACTACAACGCGCTCACCTGTGAGG  678  675  480
 L  C  V  V  C  G  D  R  A  S  G  Y  H  Y  N  A  L  T  C  E   119  119  156
```

FIG. 4 (page 1 of 3)

```
GCTGCAAAGGTTTCTTCCGAAGAAGCATTACCAAGAACGCCGTGTACAAGTGTAAGAACG       738  735  540
 G  C  K  G  F  F  R  R  S  I  T  K  N  A  V  Y  K  C  K  N        139  139  176

GGGGCAACTGCGTGATGGACATGTACATGCGCAGGAAGTGCCAGGAGTGCCGGCTAAGGA       798  795  600
 G  G  N  C  V  M  D  M  Y  M  R  R  K  C  Q  E  C  R  L  R        159  159  196
                    GTATGTATACAG  RIP14-2 specific
                     M  Y  T  G
AGTGCAGAGAGATGGGGATGTTGGCTGAAT GTTTGTTAACTGAAATCCAGTGTAAATCTA      870  867  660
 K  C  R  E  M  G  M  L  A  E  C     L  L  T  E  I  Q  C  K  S     183  183  216

AACGGCTAAGGAAAAATGTGAAGCAGCACGCTGATCAGACAGTGAATGAGGACGACAGCG      930  927  720
 K  R  L  R  K  N  V  K  Q  H  A  D  Q  T  V  N  E  D  D  S        203  203  236

AAGGGCGTGACTTGCGACAAGTGACCTCCACAACCAAGTTTTGCAGGGAGAAAACGGAAC      990  987  780
 E  G  R  D  L  R  Q  V  T  S  T  T  K  F  C  R  E  K  T  E        223  223  256

TCACGGCAGACCAGCAGACCCTCCTGGATTATATTATGGATTCGTACAACAAACAGAGAA      1050 1047  840
 L  T  A  D  Q  Q  T  L  L  D  Y  I  M  D  S  Y  N  K  Q  R        243  243  276

TGCCTCAGGAAATCACAAATAAAATCTTAAAAGAAGAATTTAGTGCAGAAGAAAATTTTC     1110 1107  900
 M  P  Q  E  I  T  N  K  I  L  K  E  E  F  S  A  E  E  N  F        263  263  296

TCATATTAACAGAAATGGCAACCAGCCATGTACAGATTCTCGTAGAATTCACAAAAAAGC    1170 1167  960
 L  I  L  T  E  M  A  T  S  H  V  Q  I  L  V  E  F  T  K  K        283  283  316

TTCCAGGGTTTCAGACACTGGACCACGAAGATCAGATTGCTTTGCTCAAAGGGTCCGCAG    1230 1227 1020
 L  P  G  F  Q  T  L  D  H  E  D  Q  I  A  L  L  K  G  S  A        303  303  336

TGGAGGCCATGTTTCTTCGTTCGGCGGAGATTTTCAATAAGAAACTTCCTGCCGGACATG    1290 1287 1080
 V  E  A  M  F  L  R  S  A  E  I  F  N  K  K  L  P  A  G  H        323  323  356

CAGACCTGTTGGAAGAAAGAATTCGAAAGAGTGGTATCTCTGATGAGTATATAACCCCGA    1350 1347 1140
 A  D  L  L  E  E  R  I  R  K  S  G  I  S  D  E  Y  I  T  P        343  343  376

TGTTCAGTTTCTATAAAAGTGTTGGAGAACTCAAAATGACTCAGGAGGAGTACGCTCTGC    1410 1407 1200
 M  F  S  F  Y  K  S  V  G  E  L  K  M  T  Q  E  E  Y  A  L        363  363  396

TCACAGCGATCGTCATCCTCTCTCCAGACAGACAATACATCAAGGACAGAGAGGCGGTGG  1470 (1453)1260
 L  T  A  I  V  I  L  S  P  D  R  Q  Y  I  K  D  R  E  A  V       383 (378)  416

AGAAGCTGCAGGAGCCCCTGCTTGATGTGCTACAAAAGCTGTGCAAGATGTACCAGCCTG  1530    -   1320
 E  K  L  Q  E  P  L  L  D  V  L  Q  K  L  C  K  M  Y  Q  P       403    -   436

AGAACCCACAGCATTTCGCCTGCCTCCTGGGTCGCCTGACGGAACTCCGGACATTCAACC (1554)   -   1380
 E  N  P  Q  H  F  A  C  L  L  G  R  L  T  E  L  R  T  F  N     (411)   -   456

ATCACCACGCTGAGATGCTGATGTCTTGGAGAGTGAATGATCACAAGTTCACCCCGCTCC    -      -   1440
 H  H  H  A  E  M  L  M  S  W  R  V  N  D  H  K  F  T  P  L      -      -    476

TCTGTGAGATCTGGGATGTGCAGTGATGGACACCAGTGGGGCTGGCTCCTTGTCCTCCTC    -      -   1500
 L  C  E  I  W  D  V  Q  *                                       -      -    484
```

FIG. 4 (page 2 of 3)

```
GGAACAGAAACCTTGTTTCGTTTGTACCTGGTTTCACTCAAGAATCTCAATGAATATTTA    -    -    1560
TGTGGCAATTATACACCTCCCACGGTTGTAAATACAGACTAGATAGAACTGCTTTCCCCA    -    -    1620
CACTGTATTTTACAAGGCTTCAGGAAACCCCACTGGCATGCCCTTTTGGCCTAATTAAAT    -    -    1680
CAATTGTTACTTCAATTCTATCTACTGAGCTAGGGGCATATTATTCTTCATTCGACAATA    -    -    1740
TTATATATATTTTATAAAGTTGAGCTGTTTTCAACTGAGACAATAAA                -    -    1787
```

FIG. 4 (page 3 of 3)

```
GCCAGGGCAACAGAGTCGGAGACCCCCTGCCACCCCCCTCCCGATCGCCGGTGCAGTCAT  -71

GAGCCCCGCCTCCCCCTGGTGCACGGAGAGGGGCGGGGCCTGGAACAAGCAGGCTGCTTC  -11

GTGACCCACTATGTCTTCCCCCACAAGTTCTCTGGACACTCCCGTGCCTGGGAATGGTTC   50
         M  S  S  P  T  S  S  L  D  T  P  V  P  G  N  G  S    17

TCCTCAGCCCAGTACCTCCGCCACGTCACCCACTATTAAGGAAGAGGGGCAGGAGACTGA  110
 P  Q  P  S  T  S  A  T  S  P  T  I  K  E  E  G  Q  E  T  D    37

TCCTCCTCCAGGCTCTGAAGGGTCCAGCTCTGCCTACATCGTGGTCATCTTAGAGCCAGA  170
 P  P  P  G  S  E  G  S  S  S  A  Y  I  V  V  I  L  E  P  E    57

GGATGAGCCTGAGCGCAAGCGGAAGAAGGGGCCGGCCCCGAAGATGCTGGGCCATGAGCT  230
 D  E  P  E  R  K  R  K  K  G  P  A  P  K  M  L  G  H  E  L    77

GTGCCGCGTGTGCGGAGACAAGGCTTCGGGCTTCCACTACAACGTGCTCAGCTGTGAAGG  290
 C  R  V  C  G  D  K  A  S  G  F  H  Y  N  V  L  S  C  E  G    97

CTGCAAAGGCTTCTTCCGGCGCAGTGTGGTCCACGGTGGGGCCGGGCGCTATGCCTGTCG  350
 C  K  G  F  F  R  R  S  V  V  H  G  G  A  G  R  Y  A  C  R   117

GGGCAGCGGAACCTGCCAGATGGATGCCTTCATGCGGCGCAAGTGCCAGCTCTGCCGGCT  410
 G  S  G  T  C  Q  M  D  A  F  M  R  R  K  C  Q  L  C  R  L   137

GCGCAAGTGCAAGGAGGCTGGCATGCGGGAGCAGTGCGTGCTCTCTGAGGAGCAGATTCG  470
 R  K  C  K  E  A  G  M  R  E  Q  C  V  L  S  E  E  Q  I  R   157

GAAGAAAAGGATTCAGAAGCAGCAACAGCAGCAGCCACCACCCCCATCTGAGCCAGCAGC  530
 K  K  R  I  Q  K  Q  Q  Q  Q  Q  P  P  P  P  S  E  P  A  A   177

CAGCAGCTCAGGCCGGCCAGCGGCCTCCCCTGGCACTTCGGAAGCAAGCAGCCAGGGCTC  590
 S  S  S  G  R  P  A  A  S  P  G  T  S  E  A  S  S  Q  G  S   197

CGGGGAAGGAGAGGGCATCCAGCTGACCGCGGCTCAGGAGCTGATGATCCAGCAGTTAGT  650
 G  E  G  E  G  I  Q  L  T  A  A  Q  E  L  M  I  Q  Q  L  V   217

TGCCGCGCAGCTGCAGTGCAACAAACGATCTTTCTCCGACCAGCCCAAAGTCACGCCCTG  710
 A  A  Q  L  Q  C  N  K  R  S  F  S  D  Q  P  K  V  T  P  W   237

GCCCCTGGGTGCAGACCCTCAGTCCCGAGATGCCCGTCAGCAACGCTTTGCCCACTTCAC  770
 P  L  G  A  D  P  Q  S  R  D  A  R  Q  Q  R  F  A  H  F  T   257

CGAGCTAGCCATCATCTCGGTCCAGGAGATTGTGGACTTTGCCAAGCAGGTGCCAGGGTT  830
 E  L  A  I  I  S  V  Q  E  I  V  D  F  A  K  Q  V  P  G  F   277

CTTGCAGTTGGGCCGGGAGGACCAGATCGCCCTCCTGAAGGCGTCCACCATTGAGATCAT  890
 L  Q  L  G  R  E  D  Q  I  A  L  L  K  A  S  T  I  E  I  M   297

GTTGCTAGAAACAGCCAGACGCTACAACCACGAGACAGAATGCATCACGTTCCTGAAGGA  950
 L  L  E  T  A  R  R  Y  N  H  E  T  E  C  I  T  F  L  K  D   317
```

FIG. 5 (page 1 of 2)

```
CTTCACCTACAGCAAGGACGACTTCCACCGTGCAGGCTTGCAGGTGGAATTCATCAATCC  1010
 F  T  Y  S  K  D  D  F  H  R  A  G  L  Q  V  E  F  I  N  P   337

CATCTTCGAGTTCTCGCGGGCCATGCGGCGGCTGGGCCTGGACGATGCAGAGTATGCCTT  1070
 I  F  E  F  S  R  A  M  R  R  L  G  L  D  D  A  E  Y  A  L   357

GCTTATCGCCATCAACATCTTCTCAGCCGATCGGCCTAATGTGCAGGAGCCCAGCCGTGT  1130
 L  I  A  I  N  I  F  S  A  D  R  P  N  V  Q  E  P  S  R  V   377

GGAGGCCCTGCAGCAGCCCTACGTGGAGGCGCTCCTCTCCTACACGAGGATCAAGCGCCC  1190
 E  A  L  Q  Q  P  Y  V  E  A  L  L  S  Y  T  R  I  K  R  P   397

ACAGGACCAGCTCCGCTTCCCACGCATGCTCATGAAGCTGGTGAGCCTGCGCACCCTCAG  1250
 Q  D  Q  L  R  F  P  R  M  L  M  K  L  V  S  L  R  T  L  S   417

CTCCGTGCACTCGGAGCAGGTCTTTGCATTGCGACTCCAGGACAAGAAGCTGCCGCCCTT  1310
 S  V  H  S  E  Q  V  F  A  L  R  L  Q  D  K  K  L  P  P  L   437

GCTGTCCGAGATCTGGGATGTGCACGAGTAGGGGCAGCCACAAGTGCCCCAGCCTTGGTG  1370
 L  S  E  I  W  D  V  H  E  *                                  446

GTGTCTTCTTGAAGATGGACTCTTCACCTCTCCTCCTGGGGTGGGAGGACATTGTCACGG  1430

CCCAGTCCCTCGGGCTCAGCCTCAAACTCAGCGGCAGTTGGCACTAAGAAGGCCCCACCC  1490

CACCCATTGAGTCTTCCAAGAGTGGTGAGGGTCACAGGTCCTAGCCTCTGACCGTTCCCA  1550

GCTGCCCTCCCACCCACGCTTACACCTCAGCCTACCACACCATGCACCTTGAGTGGAGAG  1610

AGGTTAGGGCAGGTGGCCCCCCACAGTTGGGAGACCACAGGCCCTCTCTTCTGCCCCTTT  1670

TATTTAATAAAAAAACAAAAATAAAGTTTGAGTACAAGCCAAAAAAAAAAAAAAAAAAAA  1730
```

FIG. 5 (page 2 of 2)

```
        TCTCCAAGTTGTGGCTTTCAGAGGAAGGATCTGGAAACAAGCAGTTGTGTCAGTATAAAG
    12  ---------+---------+---------+---------+---------+---------+-  71
        AGAGGTTCAACACCGAAAGTCTCCTTCCTAGACCTTTGTTCGTCAACACAGTCATATTTC c         S  P  S  C  G  F  Q  R  K  D  L  E  T  S  S  C  V  S  I  K   -

AAGAAGCGTAGACTTGAGGACTTACTCATAGTGATATCCGATAGCGATGGAGAGGAAACA
    72  ---------+---------+---------+---------+---------+---------+-  131
        TTCTTCGCATCTGAACTCCTGAATGAGTATCACTATAGGCTATCGCTACCTCTCCTTTGT c         K  K  R  R  L  E  D  L  L  I  V  I  S  D  S  D  G  E  E  T   -

AAAGAGGAGAATGGATTGCAGAAAACGAAGACAAAACAGTCGAACAGATCAAAGTGTTTG
   132  ---------+---------+---------+---------+---------+---------+-  191
        TTTCTCCTCTTACCTAACGTCTTTTGCTTCTGTTTTGTCAGCTTGTCTAGTTTCACAAAC c         K  E  E  N  G  L  Q  K  T  K  T  K  Q  S  N  R  S  K  C  L   -

GCTAAAAGAAAAGTTGCACACATGTCAGAAGAAGAACAATTTGCTTTGGCTCTCAAGATG
   192  ---------+---------+---------+---------+---------+---------+-  251
        CGATTTTCTTTTCAACGTGTGTACAGTCTTCTTCTTGTTAAACGAAACCGAGAGTTCTAC c         A  K  R  K  V  A  H  M  S  E  E  E  Q  F  A  L  A  L  K  M   -

AGTGAGCAGGAAGCTAGGGAGGTGAATAACCAGGAGGAGAAAGAAGAGGAGCTCTTGCGG
   252  ---------+---------+---------+---------+---------+---------+-  311
        TCACTCGTCCTTCGATCCCTCCACTTATTGGTCCTCCTCTTTCTTCTCCTCGAGAACGCC c         S  E  Q  E  A  R  E  V  N  N  Q  E  E  K  E  E  E  L  L  R   -

AAAGCCATTGCTGAAAGCCTGAATAGTTGCTGGTCTTCTGCTGCTTCTGCTACCAGATCT
   312  ---------+---------+---------+---------+---------+---------+-  371
        TTTCGGTAACGACTTTCGGACTTATCAACGACCAGAAGACGACGAAGACGATGGTCTAGA c         K  A  I  A  E  S  L  N  S  C  W  S  S  A  A  S  A  T  R  S   -

CGACCTCTGGCTGCTGAACTATCTTCACATTCCCATCAAGAGAACACCAAAGACTCTGGG
   372  ---------+---------+---------+---------+---------+---------+-  431
        GCTGGAGACCGACGACTTGATAGAAGTGTAAGGGTAGTTCTCTTGTGGTTTCTGAGACCC c         R  P  L  A  A  E  L  S  S  H  S  H  Q  E  N  T  K  D  S  G   -

ACCACTGAAGGCGTATGGCAGCTGGTACCTCCATCACTGTGTAAAGGCTCACATGTCAGT
   432  ---------+---------+---------+---------+---------+---------+-  491
        TGGTGACTTCCGCATACCGTCGACCATGGAGGTAGTGACACATTTCCGAGTGTACAGTCA c         T  T  E  G  V  W  Q  L  V  P  P  S  L  C  K  G  S  H  V  S   -

CAGGGAAACGAGGCTGAGCAAAGAAAGGAGCCCTGGGAcCACAATGAAAACACTGAAGAG
   492  ---------+---------+---------+---------+---------+---------+-  551
        GTCCCTTTGCTCCGACTCGTTTCTTTCCTCGGGACCCTgGTGTTACTTTTGTGACTTCTC c         Q  G  N  E  A  E  Q  R  K  E  P  W  D  H  N  E  N  T  E  E   -

GAGCCGGTCTCTGGCAGCTCAGGAAGCTGGGACCAGTCAAGCCAGCCAGTGTTTGAGAAT
   552  ---------+---------+---------+---------+---------+---------+-  611
        CTCGGCCAGAGACCGTCGAGTCCTTCGACCCTGGTCAGTTCGGTCGGTCACAAACTCTTA
```

```
c     E  P  V  S  G  S  S  G  S  W  D  Q  S  S  Q  P  V  F  E  N    -

GAGAACGTTAAATGTTTTGACAGATGTACTGGCCACTTGGCTGAGCACACACAGTGTGGG
  612 --------+---------+---------+---------+---------+---------+-  671
      CTCTTGCAATTTACAAAACTGTCTACATGACCGGTGAACCGACTCGTGTGTGTCACACCC c     E  N  V  K  C  F  D  R  C  T  G  H  L  A  E  H  T  Q  C  G    -

AAGCCACAGGAAAGTACTGGGAGTGGTTATGCTTTTTCCAAAGCTGTCCAGGGTAGGGGG
  672 --------+---------+---------+---------+---------+---------+-  731
      TTCGGTGTCCTTTCATGACCCTCACCAATACGAAAAAGGTTTCGACAGGTCCCATCCCCC c     K  P  Q  E  S  T  G  S  G  Y  A  F  S  K  A  V  Q  G  R  G    -

GACACGTCTAGGCAATGCCTTCCTATCCCAGCAGACACAAAAGGTCTCCAGGACACTGGG
  732 --------+---------+---------+---------+---------+---------+-  791
      CTGTGCAGATCCGTTACGGAAGGATAGGGTCGTCTGTGTTTTCCAGAGGTCCTGTGACCC c     D  T  S  R  Q  C  L  P  I  P  A  D  T  K  G  L  Q  D  T  G    -

GGCACTGTGCACTACTACTGGGGTATTCCATTCTGCCCTGCTGGAGTAGATCCCAATCAA
  792 --------+---------+---------+---------+---------+---------+-  851
      CCGTGACACGTGATGATGACCCCATAAGGTAAGACGGGACGACCTCATCTAGGGTTAGTT c     G  T  V  H  Y  Y  W  G  I  P  F  C  P  A  G  V  D  P  N  Q    -

TACACCAATGTCATTCTCTGCCAGTTAGAGGTTTATCAGAAGAGCCTGAAAATGGCTCAG
  852 --------+---------+---------+---------+---------+---------+-  911
      ATGTGGTTACAGTAAGAGACGGTCAATCTCCAAATAGTCTTCTCGGACTTTTACCGAGTC c     Y  T  N  V  I  L  C  Q  L  E  V  Y  Q  K  S  L  K  M  A  Q    -

AGACAGCTTGTTAAAAAAAGAGGGTTTGGGGAACCAGTGTTACCTAGACCTCCTTTTCTG
  912 --------+---------+---------+---------+---------+---------+-  971
      TCTGTCGAACAATTTTTTTCTCCCAAACCCCTTGGTCACAATGGATCTGGAGGAAAAGAC c     R  Q  L  V  K  K  R  G  F  G  E  P  V  L  P  R  P  P  F  L    -

ATCCAGAATGAATGTGGCCAAGAAGATCAGACTAGTGACAAAAATGAAGGCATCTCAGAA
  972 --------+---------+---------+---------+---------+---------+- 1031
      TAGGTCTTACTTACACCGGTTCTTCTAGTCTGATCACTGTTTTTACTTCCGTAGAGTCTT c     I  Q  N  E  C  G  Q  E  D  Q  T  S  D  K  N  E  G  I  S  E    -

GATATGGGAGATGAAGCCAAAGAGGAAAGGCAGGAATCTAGGGCATCTGTCTGGCACTCA
 1032 --------+---------+---------+---------+---------+---------+- 1091
      CTATACCCTCTACTTCGGTTTCTCCTTTCCGTCCTTAGATCCCGTAGACAGACCGTGAGT c     D  M  G  D  E  A  K  E  E  R  Q  E  S  R  A  S  V  W  H  S    -

GAAACCAAGGATTTTCAAAAAAGTCCAATTAAAAGCTTGAAACAGAAACTTTTGTTGGAG
 1092 --------+---------+---------+---------+---------+---------+- 1151
      CTTTGGTTCCTAAAAGTTTTTTCAGGTTAATTTTCGAACTTTGTCTTTGAAAACAACCTC c     E  T  K  D  F  Q  K  S  P  I  K  S  L  K  Q  K  L  L  L  E    -

GAAGAACCAACAACCAGTCGTGGTCAGTCTTCCCAAGGTCTGTTTGTTGAAGAAACCTCT
 1152 --------+---------+---------+---------+---------+---------+- 1211
      CTTCTTGGTTGTTGGTCAGCACCAGTCAGAAGGGTTCCAGACAAACAACTTCTTTGGAGA c     E  E  P  T  T  S  R  G  Q  S  S  Q  G  L  F  V  E  E  T  S    -
```

FIG. 10 (page 2 of 4)

```
            GAAGAAGGTCTGAAGAGTTCGGAAGGAGACAACTCTGTGCCCACCACGCAAAGCATTGCA
     1212   ------------------------------------------------------------   1271
            CTTCTTCCAGACTTCTCAAGCCTTCCTCTGTTGAGACACGGGTGGTGCGTTTCGTAACGT c         E  E  G  L  K  S  S  E  G  D  N  S  V  P  T  T  Q  S  I  A    -

GCTTTGACCAGTAAGAGAAGTTTAGTTCTTATGCCGGAAAGTTCTGCAGAAGAAATCACT
     1272   ------------------------------------------------------------   1331
            CGAAACTGGTCATTCTCTTCAAATCAAGAATACGGCCTTTCAAGACGTCTTCTTTAGTGA c         A  L  T  S  K  R  S  L  V  L  M  P  E  S  S  A  E  E  I  T    -

GTTTGCCCTGAGACACAGTTAAGTTTCCTTGAACCCCTTGACCTCAATAGAGAAGACTCT
     1332   ------------------------------------------------------------   1391
            CAAACGGGACTCTGTGTCAATTCAAAGGAACTTGGGGAACTGGAGTTATCTCTTCTGAGA c         V  C  P  E  T  Q  L  S  F  L  E  P  L  D  L  N  R  E  D  S    -

CCAGATAGCAGAGAGCTCCCCATTGAAGTAAGGATGGCAGTGGGCGATAAGCAGGTTGCT
     1392   ------------------------------------------------------------   1451
            GGTCTATCGTCTCTCGAGGGGTAACTTCATTCCTACCGTCACCCGCTATTCGTCCAACGA c         P  D  S  R  E  L  P  I  E  V  R  M  A  V  G  D  K  Q  V  A    -

AATAGGGAAGATTGTATGAAGGAAAACCCTCCTCCTGCAGTCTCATCTAGTACCCGGGTA
     1452   ------------------------------------------------------------   1511
            TTATCCCTTCTAACATACTTCCTTTTGGGAGGAGGACGTCAGAGTAGATCATGGGCCCAT c         N  R  E  D  C  M  K  E  N  P  P  P  A  V  S  S  S  T  R  V    -

TCCTGCCCACTGTGTAACCAAGACTTTCCTCCCACAAAGATTGAACAGCATGCCATGTAC
     1512   ------------------------------------------------------------   1571
            AGGACGGGTGACACATTGGTTCTGAAAGGAGGGTGTTTCTAACTTGTCGTACGGTACATG c         S  C  P  L  C  N  Q  D  F  P  P  T  K  I  E  Q  H  A  M  Y    -

TGCAATGGTCTGATGGAGCAGGAAACAGTGTTGACTCGGAGACGAAGAGAGGCCAAGAAC
     1572   ------------------------------------------------------------   1631
            ACGTTACCAGACTACCTCGTCCTTTGTCACAACTGAGCCTCTGCTTCTCTCCGGTTCTTG c         C  N  G  L  M  E  Q  E  T  V  L  T  R  R  R  R  E  A  K  N    -

AAGAGTGACGGTCGGACAGCTGCACAGCCGGCTCTGGATGCCAACAGGAAGGAGAAGTGT
     1632   ------------------------------------------------------------   1691
            TTCTCACTGCCAGCCTGTCGACGTGTCGGCCGAGACCTACGGTTGTCCTTCCTCTTCACA c         K  S  D  G  R  T  A  A  Q  P  A  L  D  A  N  R  K  E  K  C    -

TATCTATGTAAGTCCCTGGTTCCACTTGGGGAGTATCAGTGCCATGTGGAGGCCTGTCTC
     1692   ------------------------------------------------------------   1751
            ATAGATACATTCAGGGACCAAGGTGAACCCCTCATAGTCACGGTACACCTCCGGACAGAG c         Y  L  C  K  S  L  V  P  L  G  E  Y  Q  C  H  V  E  A  C  L    -

CAGCTTGCAAAGGTTGACAGAGAAGATGGGATTGAAGGGACAAGGAGACCAAGGGTGTGT
     1752   ------------------------------------------------------------   1811
            GTCGAACGTTTCCAACTGTCTCTTCTACCCTAACTTCCCTGTTCCTCTGGTTCCCACACA c         Q  L  A  K  V  D  R  E  D  G  I  E  G  T  R  R  P  R  V  C    -

GCACCTGTGGAGGGGAAACAACAGCAGCGGCTGAAGAAGTCAAAGGACAAAGGCCATAGT
```

FIG. 10 (page 3 of 4)

```
     1812 --------+---------+---------+---------+---------+---------+- 1871
          CGTGGACACCTCCCCTTTGTTGTCGTCGCCGACTTCTTCAGTTTCCTGTTTCCGGTATCA c         A   P   V   E   G   K   Q   Q   Q   R   L   K   K   S   K   D   K   G   H   S    -

CAAGGCCGACTCCTCAGTCTCTTGGAGCAGTCTGAGCATAGGACCACAGGTGTAGAGAAA
     1872 --------+---------+---------+---------+---------+---------+- 1931
          GTTCCGGCTGAGGAGTCAGAGAACCTCGTCAGACTCGTATCCTGGTGTCCACATCTCTTT c         Q   G   R   L   L   S   L   L   E   Q   S   E   H   R   T   T   G   V   E   K    -

AAACCCAAGTATTCGGAAGTAAGAACCTTCAGGATGCCCTCACCAGAGGTGGAAGAGGCT
     1932 --------+---------+---------+---------+---------+---------+- 1991
          TTTGGGTTCATAAGCCTTCATTCTTGGAAGTCCTACGGGAGTGGTCTCCACCTTCTCCGA c         K   P   K   Y   S   E   V   R   T   F   R   M   P   S   P   E   V   E   E   A    -

AGCTGCAGCAGAGAGATGCAGAGTACCCTCTCACAGCTCAACTTAAATGAGTCTCCCATC
     1992 --------+---------+---------+---------+---------+---------+- 2051
          TCGACGTCGTCTCTCTACGTCTCATGGGAGAGTGTCGAGTTGAATTTACTCAGAGGGTAG c         S   C   S   R   E   M   Q   S   T   L   S   Q   L   N   L   N   E   S   P   I    -

AAGTCTTTTGTTCCTGTTTCAGAAGCTACAAATTGCTTAGTGGACTTTAAAGAACAGTTT
     2052 --------+---------+---------+---------+---------+---------+- 2111
          TTCAGAAAACAAGGACAAAGTCTTCGATGTTTAACGAATCACCTGAAATTTCTTGTCAAA c         K   S   F   V   P   V   S   E   A   T   N   C   L   V   D   F   K   E   Q   F    -

GCTTTCCGGTCACGAACTAAATCAGGCAGGGAAAGGAGGAGAAAATCTTGAATTTCTTGA
     2112 --------+---------+---------+---------+---------+---------+- 2171
          CGAAAGGCCAGTGCTTGATTTAGTCCGTCCCTTTCCTCCTCTTTTAGAACTTAAAGAACT c         A   F   R   S   R   T   K   S   G   R   E   R   R   R   K   S   *

GACTGGAAGGTTGACCAGAACACACATCGTTGGGTTGATCGTGTTCATTAAGTATAGTGG
     2172 --------+---------+---------+---------+---------+---------+- 2231
          CTGACCTTCCAACTGGTCTTGTGTGTAGCAACCCAACTAGCACAAGTAATTCATATCACC

TCTCTAGTTTGTGGTGAGAGTTCTGACCCTGTTGTTATCACCACCAGCACCCATTCAGTA
     2232 --------+---------+---------+---------+---------+---------+- 2291
          AGAGATCAAACACCACTCTCAAGACTGGGACAACAATAGTGGTGGTCGTGGGTAAGTCAT

TCCTGGCTTTATATTTTATAAGATCAGTTCAGACAACTGTGAATATTATTCTGTTTGAAT
     2292 --------+---------+---------+---------+---------+---------+- 2351
          AGGACCGAAATATAAAATATTCTAGTCAAGTCTGTTGACACTTATAATAAGACAAACTTA

TTGCTTATAGTTAAAATTTAAATATATTTATCTTTGTATGAAAAAAAA
     2352 --------+---------+---------+---------+---------+
          AACGAATATCAATTTTAAATTTATATAAATAGAAACATACTTTTTTTT
```

FIG. 10 (page 4 of 4)

```
        GGATGCCCTGGCTGCTCTTGTGGATGCTGCAGCTTCTGCACCCCAGATGGATGTTTCCAA
   901  ---------+---------+---------+---------+---------+---------+  960
        CCTACGGGACCGACGAGAACACCTACGACGTCGAAGACGTGGGGTCTACCTACAAAGGTT b        D  A  L  A  A  L  V  D  A  A  A  S  A  P  Q  M  D  V  S  K  -

AACAAAAGAGAGTAAGCATGAAGCTGCCAGGTTAGAAGAAAATTTGAGAAGCAGGTCAGC
   961  ---------+---------+---------+---------+---------+---------+ 1020
        TTGTTTTCTCTCATTCGTACTTCGACGGTCCAATCTTCTTTTAAACTCTTCGTCCAGTCG b        T  K  E  S  K  H  E  A  A  R  L  E  E  N  L  R  S  R  S  A  -

AGCAGTTAGTGAACAGCAGCAGCTAGAGCAGAAAAACCTGGAGGTGGAGAAGAGATCTGT
  1021  ---------+---------+---------+---------+---------+---------+ 1080
        TCGTCAATCACTTGTCGTCGTCGATCTCGTCTTTTTGGACCTCCACCTCTTCTCTAGACA b        A  V  S  E  Q  Q  Q  L  E  Q  K  N  L  E  V  E  K  R  S  V  -

TCAGTGTGTGTGCACTTCTTCAGCCCTTCCAAGTGGCAAGGCCCAGCCTCATGCCTCAGT
  1081  ---------+---------+---------+---------+---------+---------+ 1140
        AGTCACACACACGTGAAGAAGTCGGGAAGGTTCACCGTTCCGGGTCGGAGTACGGAGTCA b        Q  C  V  C  T  S  S  A  L  P  S  G  K  A  Q  P  H  A  S  V  -

AGTGTATTCTGAGGCTGGGAAAGATAAAGGGCCTCCTCCAAAATCCAGATATGAGGAAGA
  1141  ---------+---------+---------+---------+---------+---------+ 1200
        TCACATAAGACTCCGACCCTTTCTATTTCCCGGAGGAGGTTTTAGGTCTATACTCCTTCT b        V  Y  S  E  A  G  K  D  K  G  P  P  P  K  S  R  Y  E  E  E  -

GCTAAGGACCCGAGGGAAGACTACCATTACTGCAGCTAACTTCATAGACGTGACCATCAC
  1201  ---------+---------+---------+---------+---------+---------+ 1260
        CGATTCCTGGGCTCCCTTCTGATGGTAATGACGTCGATTGAAGTATCTGCACTGGTAGTG b        L  R  T  R  G  K  T  T  I  T  A  A  N  F  I  D  V  T  I  T  -

CCGGCAAATTGCCTCGGACAAGGATGCGAGGGAACGTGGCTCTCAAAGTTCAGACTCTTC
  1261  ---------+---------+---------+---------+---------+---------+ 1320
        GGCCGTTTAACGGAGCCTGTTCCTACGCTCCCTTGCACCGAGAGTTTCAAGTCTGAGAAG b        R  Q  I  A  S  D  K  D  A  R  E  R  G  S  Q  S  S  D  S  S  -

TAGTAGCTTGTCTTCTCACAGGTATGAAACGGCTAGTGATGCCATTGAGGTGATAAGTCC
  1321  ---------+---------+---------+---------+---------+---------+ 1380
        ATCATCGAACAGAAGAGTGTCCATACTTTGCCGATCACTACGGTAACTCCACTATTCAGG b        S  S  L  S  S  H  R  Y  E  T  A  S  D  A  I  E  V  I  S  P  -

CGCCAGCTCACCTGCACCACCCCAGGAAAAGCCACAGGCCTATCAGCCAGACATGGTTAA
  1381  ---------+---------+---------+---------+---------+---------+ 1440
        GCGGTCGAGTGGACGTGGTGGGGTCCTTTTCGGTGTCCGGATAGTCGGTCTGTACCAATT b        A  S  S  P  A  P  P  Q  E  K  P  Q  A  Y  Q  P  D  M  V  K  -
```

FIG. 11 (page 1 of 4)

```
        GGCAAATCAAGCAGAAAATGAGTCCACTCGACAGTATGAAGGTCCACTGCATCATTATCG
   1441 ------------------------------------------------------------ 1500
        CCGTTTAGTTCGTCTTTTACTCAGGTGAGCTGTCATACTTCCAGGTGACGTAGTAATAGC b        A  N  Q  A  E  N  E  S  T  R  Q  Y  E  G  P  L  H  H  Y  R  -

GTCCCAGCAGGAATCACCATCTCCACAGCAACAGCCACCACTGCCCCCATCTTCCCAGTC
   1501 ------------------------------------------------------------ 1560
        CAGGGTCGTCCTTAGTGGTAGAGGTGTCGTTGTCGGTGGTGACGGGGGTAGAAGGGTCAG b           S  Q  Q  E  S  P  S  P  Q  Q  Q  P  P  L  P  P  S  S  Q  S -

AGAGGGAATGGGACAGGTGCCCAGGACCCATCGACTGATCACACTTGCTGACCACATCTG
   1561 ------------------------------------------------------------ 1620
        TCTCCCTTACCCTGTCCACGGGTCCTGGGTAGCTGACTAGTGTGAACGACTGGTGTAGAC b           E  G  M  G  Q  V  P  R  T  H  R  L  I  T  L  A  D  H  I  C -

TCAAATTATCACACAAGATTTTGCTAGAAATCAAGTTCCCTCGCAGCCTTCTACTTCTAC
   1621 ------------------------------------------------------------ 1680
        AGTTTAATAGTGTGTTCTAAAACGATCTTTAGTTCAAGGGAGCGTCGGAAGATGAAGATG b           Q  I  I  T  Q  D  F  A  R  N  Q  V  P  S  Q  P  S  T  S  T -

ATTCCAAACTTCACCATCTGCTTTGTCATCCACACCTGTAAGAACTAAAACCTCAAGCCG
   1681 ------------------------------------------------------------ 1740
        TAAGGTTTGAAGTGGTAGACGAAACAGTAGGTGTGGACATTCTTGATTTTGGAGTTCGGC b           F  Q  T  S  P  S  A  L  S  S  T  P  V  R  T  K  T  S  S  R -

CTACAGCCCAGAATCACAGTCTCAGACTGTCTTGCATCCCAGACCAGGTCCTAGAGTCTC
   1741 ------------------------------------------------------------ 1800
        GATGTCGGGTCTTAGTGTCAGAGTCTGACAGAACGTAGGGTCTGGTCCAGGATCTCAGAG b           Y  S  P  E  S  Q  S  Q  T  V  L  H  P  R  P  G  P  R  V  S -

TCCAGAAAATCTTGTGGATAAATCCCGGGGAAGCAGGCCTGGAAAATCTCCAGAGAGGAG
   1801 ------------------------------------------------------------ 1860
        AGGTCTTTTAGAACACCTATTTAGGGCCCCTTCGTCCGGACCTTTTAGAGGTCTCTCCTC b           P  E  N  L  V  D  K  S  R  G  S  R  P  G  K  S  P  E  R  S -

TCATATCCCATCAGAGCCCTATGAGCCCATCTCCCCACCCCAAGGCCCTGCTGTGCATGA
   1861 ------------------------------------------------------------ 1920
        AGTATAGGGTAGTCTCGGGATACTCGGGTAGAGGGGTGGGGTTCCGGGACGACACGTACT b           H  I  P  S  E  P  Y  E  P  I  S  P  P  Q  G  P  A  V  H  E -

GAAGCAGGACAGCATGTTGCTCTTGTCACAGAGGGGAGTGGACCCTGCTGAGCAAAGGAG
   1921 ------------------------------------------------------------ 1980
        CTTCGTCCTGTCGTACAACGAGAACAGTGTCTCCCCTCACCTGGGACGACTCGTTTCCTC b           K  Q  D  S  M  L  L  L  S  Q  R  G  V  D  P  A  E  Q  R  S -

TGATTCTCGATCACCAGGAAGTATAAGCTACTTGCCTTCATTCTTCACCAAGCTTGAAAG
   1981 ------------------------------------------------------------ 2040
        ACTAAGAGCTAGTGGTCCTTCATATTCGATGAACGGAAGTAAGAAGTGGTTCGAACTTTC b           D  S  R  S  P  G  S  I  S  Y  L  P  S  F  F  T  K  L  E  S -

CACATCACCCATGGTTAAATCAAAGAAACAGGAAATTTTTCGTAAGTTGAACTCTTCTGG
```

FIG. 11 (page 2 of 4)

```
      2041 ---------+---------+---------+---------+---------+---------+ 2100
           GTGTAGTGGGTACCAATTTAGTTTCTTTGTCCTTTAAAAAGCATTCAACTTGAGAAGACC b        T  S  P  M  V  K  S  K  K  Q  E  I  F  R  K  L  N  S  S  G  -

TGGAGGTGACTCTGATATGGCAGCTGCTCAGCCAGGAACAGAGATCTTCAATCTGCCAGC
      2101 ---------+---------+---------+---------+---------+---------+ 2160
           ACCTCCACTGAGACTATACCGTCGACGAGTCGGTCCTTGTCTCTAGAAGTTAGACGGTCG b        G  G  D  S  D  M  A  A  A  Q  P  G  T  E  I  F  N  L  P  A  -

AGTTACCACATCAGGTGCAGTGAGCTCAAGAAGCCATTCTTTTGCTGATCCCGCCAGTAA
      2161 ---------+---------+---------+---------+---------+---------+ 2220
           TCAATGGTGTAGTCCACGTCACTCGAGTTCTTCGGTAAGAAAACGACTAGGGCGGTCATT b        V  T  T  S  G  A  V  S  S  R  S  H  S  F  A  D  P  A  S  N  -

CCTTGGTCTAGAAGACATCATCAGAAAGGCTCTCATGGGAAGTTTTGATGATAAAGTTGA
      2221 ---------+---------+---------+---------+---------+---------+ 2280
           GGAACCAGATCTTCTGTAGTAGTCTTTCCGAGAGTACCCTTCAAAACTACTATTTCAACT b        L  G  L  E  D  I  I  R  K  A  L  M  G  S  F  D  D  K  V  E  -

AGATCATGGTGTTGTCATGTCCCATCCTGTGGGCATTATGCCTGGTAGTGCCAGCACCTC
      2281 ---------+---------+---------+---------+---------+---------+ 2340
           TCTAGTACCACAACAGTACAGGGTAGGACACCCGTAATACGGACCATCACGGTCGTGGAG b        D  H  G  V  V  M  S  H  P  V  G  I  M  P  G  S  A  S  T  S  -

AGTGGTGACGAGCAGCGAGGCACGGAGAGATGAAGGGGAGCCATCACCTCATGCAGGAGT
      2341 ---------+---------+---------+---------+---------+---------+ 2400
           TCACCACTGCTCGTCGCTCCGTGCCTCTCTACTTCCCCTCGGTAGTGGAGTACGTCCTCA b        V  V  T  S  S  E  A  R  R  D  E  G  E  P  S  P  H  A  G  V  -

ATGCAAACCAAAGCTGATCAACAAATCAAACAGCAGGAAGTCTAAATCTCCTATTCCTGG
      2401 ---------+---------+---------+---------+---------+---------+ 2460
           TACGTTTGGTTTCGACTAGTTGTTTAGTTTGTCGTCCTTCAGATTTAGAGGATAAGGACC b        C  K  P  K  L  I  N  K  S  N  S  R  K  S  K  S  P  I  P  G  -

GCAAAGCTATTTAGGAACTGAAAGGCCTTCTTCTGTCTCCTCTGTGCATTCAGAAGGTGA
      2461 ---------+---------+---------+---------+---------+---------+ 2520
           CGTTTCGATAAATCCTTGACTTTCCGGAAGAAGACAGAGGAGACACGTAAGTCTTCCACT b        Q  S  Y  L  G  T  E  R  P  S  S  V  S  S  V  H  S  E  G  D  -

TTACCACAGGCAGACACCAGGATGGGCATGGGAAGATCGGCCCTCTTCAACAGGTTCTAC
      2521 ---------+---------+---------+---------+---------+---------+ 2580
           AATGGTGTCCGTCTGTGGTCCTACCCGTACCCTTCTAGCCGGGAGAAGTTGTCCAAGATG b        Y  H  R  Q  T  P  G  W  A  W  E  D  R  P  S  S  T  G  S  T  -

TCAGTTCCCTTACAACCCTCTGACCATACGGATGCTCAGCAGTACACCACCTACACAGAT
      2581 ---------+---------+---------+---------+---------+---------+ 2640
           AGTCAAGGGAATGTTGGGAGACTGGTATGCCTACGAGTCGTCATGTGGTGGATGTGTCTA b        Q  F  P  Y  N  P  L  T  I  R  M  L  S  S  T  P  P  T  Q  I  -

CGCATGCGCCCCATCTGCCATCACCCAAGCAGCTCCACATCAACAGAACCGCATCTGGGA
      2641 ---------+---------+---------+---------+---------+---------+ 2700
           GCGTACGCGGGGTAGACGGTAGTGGGTTCGTCGAGGTGTAGTTGTCTTGGCGTAGACCCT
```

FIG. 11 (page 3 of 4)

```
b        A  C  A  P  S  A  I  T  Q  A  A  P  H  Q  Q  N  R  I    W  E -
     GAGGGAGCCTGCCCCGCTCCTCTCAGCGCAGTATGAGACACTGTCTGATAGTGACGACTG
2701 ---------+---------+---------+---------+---------+---------+ 2760
     CTCCCTCGGACGGGGCGAGGAGAGTCGCGTCATACTCTGTGACAGACTATCACTGCTGAC
b        R  E  P  A  P  L  L  S  A  Q  Y  E  T  L  S  D  S  D  D  * -
     AGCTGTGCGTGGGAGAGCGCTCTGGCTTTGGTTTTTATTGAAGATTTAAAAAAAAAAAAA
2761 ---------+---------+---------+---------+---------+---------+ 2820
     TCGACACGCACCCTCTCGCGAGACCGAAACCAAAAATAACTTCTAAATTaTTTTTTTTTT

AA
2821    --  2822
        TT
```

FIG. 11 (page 4 of 4)

RETINOID X RECEPTOR-INTERACTING POLYPEPTIDES AND RELATED MOLECULES AND METHODS

CROSS-REFERENCE TO RELATED APPLICATIONS

This application is a divisional of U.S. patent application Ser. No. 08/372,652, filed Jan. 13, 1995, now U.S. Pat. No. 5,932,699.

BACKGROUND OF THE INVENTION

This invention relates to receptor proteins.

This invention was made in part with Government funding, and the Government therefore has certain rights in the invention.

The retinoid X receptors (RXRs) are members of a large superfamily of intracellular hormone receptors. These proteins bind to specific DNA sequences and directly regulate transcription of target genes in response to activation by their specific ligands (Leid et al., Trends Biochem. Sci. 17:427–433, 1992; Leid et al., Cell 68:377–395, 1992; Mangelsdorf et al., Nature 345:224–229, 1990 and Yu et al., Cell 67:1251–1266, 1991). The RXRs belong to a large subgroup of the superfamily defined by a conserved subregion within the DNA binding domain. This group also includes the receptors for retinoic acid, thyroid hormone, and vitamin D as well as a number of other less well characterized proteins, called orphan receptors, that do not have known ligands. As monomers, the members of this class can bind to sequences related to the hexameric consensus AGGTCA. RXR homodimers bind to tandem repeats of this consensus separated by a single base pair (Manglesdorf et al., Cell 66:555–561, 1991), and apparently to additional elements including β-RARE (Zhang et al., Nature 358:587–591, 1992). These homodimer binding sites confer specific response to 9-cis-RA (9-cis-RA), the ligand for the RXRs. In addition, the RXRs heterodimerize with a variety of other family members, including the receptors for all-trans-retinoic acid, thyroid hormone (T3), and vitamin D. This heterodimerization strongly increases the affinity of these receptors for their specific response elements (Yu et al., Cell 67:1251–1266, 1991; Zhang et al., Nature 358: 587–591, 1992; Bugge et al., EMBO J. 11:1409–1418, 1992), and recent evidence also demonstrates that it is also required for full hormone dependent transcriptional activity of at least the thyroid hormone receptor-RXR complex.

Mammals have three genes encoding α, β, and γ isoforms of RXR (Mangelsdorf et al., Genes & Dev. 6:329–344, 1992). The expression patterns of murine RXRs (Mangelsdorf et al., Genes & Dev. 6:329–344, 1992) and homologues of RXR found in Xenopus (Blumberg et al., Proc. Natl. Acad. Sci. USA 89:2321–2325, 1992) and Drosophila (Oro et al., Nature 347:298–301, 1990) suggest that the members of the RXR family play important roles in several aspects of development and central nervous system differentiation as well as in adult physiology. Based on both their specific response to the 9-cis-RA metabolite and their heterodimerization with the RARs, it is clear that the RXRs play a central role in the broad regulatory effects of retinoids. Moreover, their heterodimeric interactions with other family members indicate that the RXRs also play a central role in response to thyroid hormone, vitamin D, and perhaps other compounds. This dual function is unique within the nuclear receptor superfamily.

SUMMARY OF THE INVENTION

In a first aspect, the invention generally features a method for determining whether a test protein is capable of interacting with a retinoid X receptor (RXR) protein. The method involves: (a) providing a host cell which contains (i) a reporter gene operably linked to a protein binding site; (ii) a first fusion gene which expresses a first fusion protein, the first fusion protein including a retinoid X receptor protein covalently bonded to a binding moiety which is capable of specifically binding to the protein binding site; and (iii) a second fusion gene which expresses a second fusion protein, the second fusion protein including the test protein covalently bonded to a gene activating moiety; and (b) determining whether the test protein increases expression of the reporter gene as an indication of its ability to interact with the retinoid X receptor protein.

In a preferred embodiment, the method further involves treating the host cell with a ligand which binds the retinoid X receptor (preferably, 9-cis-RA) and identifying a ligand-dependent interacting protein by its ability to increase expression of the reporter gene upon treatment of the cell by the ligand. In another preferred embodiment, the method further involves treating the host cell with a ligand which binds the retinoid X receptor and identifying a ligand-independent interacting protein by its ability to increase expression of the reporter gene both in the presence and in the absence of ligand treatment. In yet another preferred embodiment, the method further involves treating the host cell with a ligand which binds the retinoid X receptor and identifying a ligand-sensitive interacting protein by its ability to increase expression of the reporter gene in the absence but not in the presence of ligand treatment.

In other preferred embodiments, the gene activating moiety is the gene activating moiety of B42.

In a second aspect, the invention features a substantially pure preparation of a retinoid X receptor (RXR)-interacting protein. Preferably, the RXR-interacting protein is RIP14, RIP15, RIP110, or RIP13; or includes an amino acid sequence substantially identical to an amino acid sequence shown in any of FIGS. 4, 5, 10, and 11 (SEQ ID NOS: 1–5); is derived from a mammal, for example, a human; binds a β-RARE site in the presence of RXR; or binds an EcRE site in the presence of RXR.

The invention also features purified DNA (for example, cDNA) which includes a sequence encoding an RXR-interacting protein, preferably encoding a human RXR-interacting protein (for example, the RXR-interacting proteins RIP14 (SEQ ID NO: 6, 14), RIP15 (SEQ ID NO: 7), RIP110 (SEQ ID NO: 8), or RIP13 (SEQ ID NO: 9)); a vector and a cell which includes a purified DNA of the invention; and a method of producing a recombinant RXR-interacting protein involving providing a cell transformed with DNA encoding an RXR-interacting protein positioned for expression in the cell; culturing the transformed cell under conditions for expressing the DNA; and isolating the recombinant RXR-interacting protein. The invention further features recombinant RXR-interacting protein produced by such expression of a purified DNA of the invention.

As used herein, "reporter gene" is meant a gene whose expression may be assayed; such genes include, without limitation, lacZ, amino acid biosynthetic genes, e.g. the yeast LEU2 gene, luciferase, or the mammalian chloramphenicol transacetylase (CAT) gene. Reporter genes may be integrated into the chromosome or may be carried on autonomously replicating plasmids (e.g., yeast 2μ plasmids).

By "operably linked" is meant that a gene and a regulatory sequence(s) are connected in such a way as to permit gene expression when the appropriate molecules (e.g., transcriptional activator proteins or proteins which include transcriptional activation domains) are bound to the regulatory sequence(s).

By a "binding moiety" is meant a stretch of amino acids which is capable of directing specific polypeptide binding to a particular DNA sequence (i.e., a "protein binding site"). LexA represents a preferred DNA binding moiety in the invention. However, any other transcriptionally-inert or essentially transcriptionally-inert DNA binding domain may be substituted. The GAL4 DNA binding domain represents a somewhat less preferred DNA binding moiety for the system described herein.

By "gene activating moiety" is meant a stretch of amino acids which is capable of inducing the expression of a gene to whose control region it is bound. As used herein, a "weak gene activating moiety" is meant a stretch of amino acids which induces gene expression at a level below the level of activation effected by GAL4 activation region II (Ma and Ptashne, Cell 48:847, 1987) and is preferably at or below the level of activation effected by the B42 activation domain of Ma and Ptashne (Cell 51:113, 1987). Levels of activation may be measured using any downstream reporter gene system and comparing, in parallel assays, the level of expression stimulated by the GAL4- or B42-polypeptide with the level of expression stimulated by the polypeptide to be tested.

By "RXR-interacting protein" is meant a polypeptide which directly or indirectly physically interacts with a retinoid X receptor in the in vivo protein interaction assay described herein. Such an interaction may be hormone (or ligand) dependent or independent or may be hormone (or ligand) sensitive; it may also be transient in nature so long as the interaction is capable of producing a positive result in the interaction assay described herein. Preferably, such a polypeptide has an amino acid sequence which is at least 85%, preferably 90%, and most preferably 95% or even 99% identical to the amino acid sequence of an interacting protein described herein (e.g., RIP14, RIP15, RIP110, or RIP13) at the point of interaction with the retinoid X receptor, or at least 80% and preferably 90% identical overall.

By "substantially pure" is meant a preparation which is at least 60% by weight (dry weight) the compound of interest, i.e., an RXR-interacting protein. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

By "purified DNA" is meant DNA that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (assayed, e.g., as described herein). Preferably, such a sequence is at least 85%, more preferably 90%, and most preferably 95% identical at the amino acid level to one of the sequences of FIGS. 4, 5, 10, and 11 (SEQ ID NOS: 1–5). A "substantially identical" nucleic acid sequence codes for a substantially identical amino acid sequence as defined above.

By "transformed cell" is meant a cell into which (or into an ancestor of which) has been introduced, by means of recombinant DNA techniques, a DNA molecule encoding (as used herein) an RXR-interacting protein.

By "positioned for expression" is meant that the DNA molecule is positioned adjacent to a DNA sequence which directs transcription and translation of the sequence (i.e., facilitates the production of, e.g., an RXR-interacting protein).

By "purified antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight, antibody, e.g., RXR-interacting protein-specific antibody. A purified RXR-interacting protein antibody may be obtained, for example, by affinity chromatography using recombinantly-produced RXR-interacting protein and standard techniques.

By "specifically binds" is meant an antibody which recognizes and binds RXR-interacting protein but which does not substantially recognize and bind other molecules in a sample, e.g., a biological sample, which naturally includes RXR-interacting protein.

Other features and advantages of the invention will be apparent from the following detailed description thereof, and from the claims.

DESCRIPTION OF THE DRAWINGS

The drawings are first described.

FIG. 4 is the nucleotide (SEQ ID NO: 6, 14) and deduced amino acid sequences (SEQ ID NOS: 1, 2) of the RIP14 clone. Numbers of nucleotides and amino acids of each sequence are shown on the left side. For RIP14-1 (SEQ ID NO: 1), the sequence of Clone 6 is shown. Four amino acids unique to RIP14-2 (SEQ ID NO: 2) are also shown. The DNA binding domain (C domain) and a poly A signal are underlined. N-terminus unique to isoform 1 is shown as italicized letters and the putative initiation codons as bold letters. Because the 5' ends of the RIP14-2 clones are different, both Clone 3 and Clone 12 are shown. A 63 base pair direct repeat which occurs in the 5' end of Clone 12 is indicated as underlined and in italicized letters. The GenBank submission numbers of RIP14-1 is UO9416. The submission number of RIP14-2 Clones 3 and 12 are UO9417 and UO9418, respectively.

FIG. 5 is the nucleotide (SEQ ID NO: 7) and deduced amino acid sequences (SEQ ID NO: 3) of RIP15. The in frame termination codon in front of the initiation codon, the DNA binding domain (C domain), and a poly A signal are underlined. The GenBank submission number of this sequence is UO9419.

Figure 6:
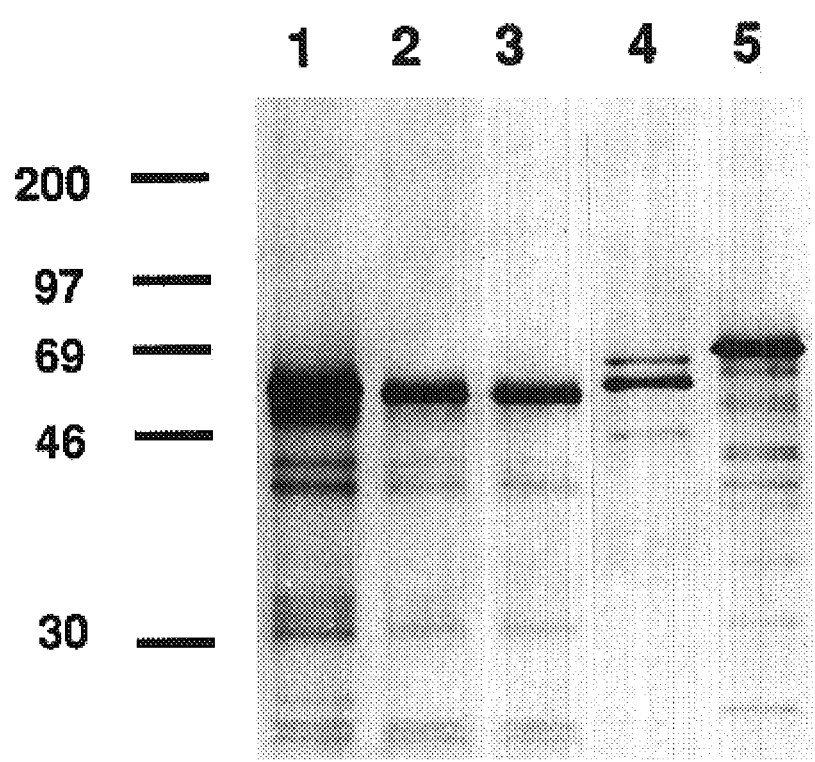

FIG. 6 is a photograph showing an SDS-polyacrylamide gel analysis of in vitro translated RIP proteins. Lane 1: RIP14-1, 2: RIP14-2 (No. 3), 3: RIP14-2 (No. 12), 4: RIP15, 5: positive control (luciferase, MW ca 69 Kd). Clone No. 15 was used for expression of RIP14-1, and the full length derivatives of both Clones No. 3 and 12 (as described herein) for RIP14-2. Molecular weight markers are shown.

Figure 7A:
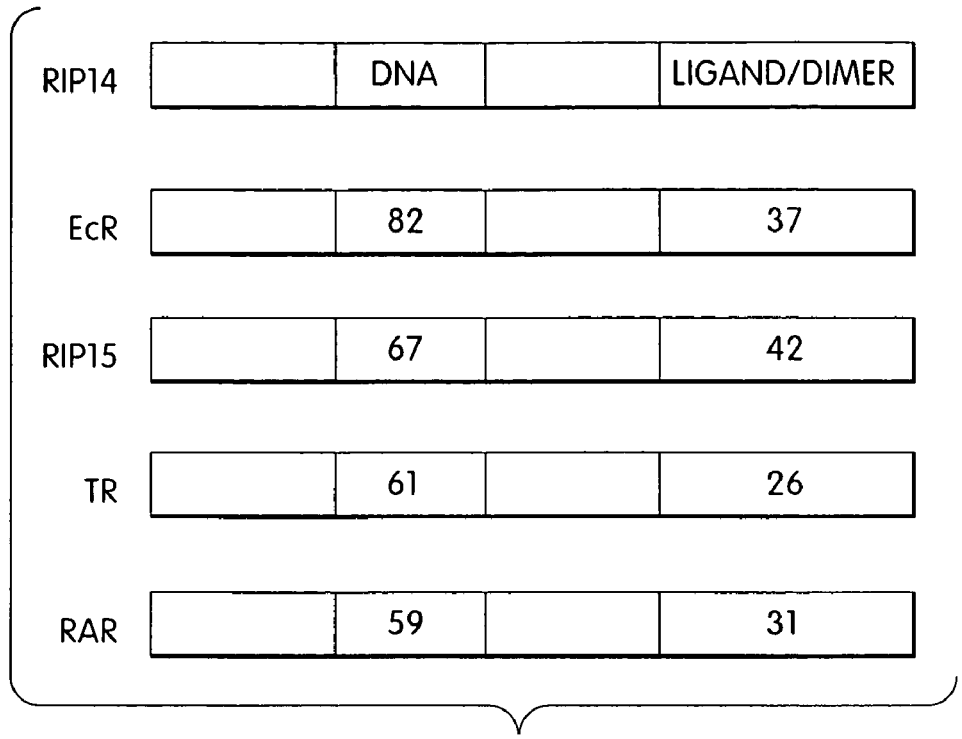
Figure 7B:
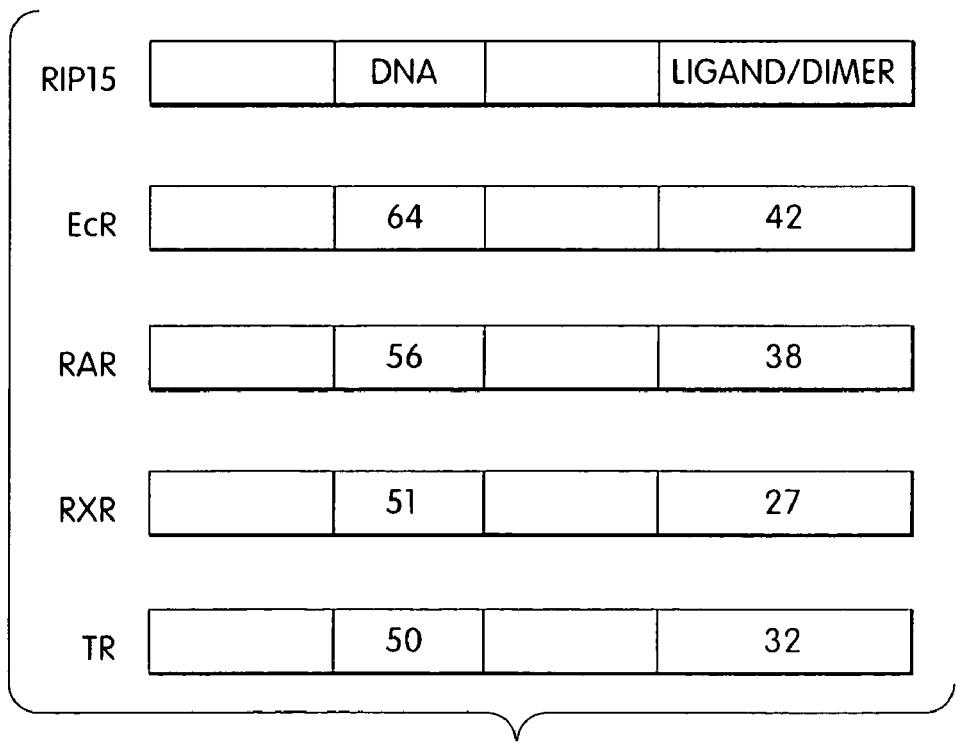

FIG. 7 is a schematic diagram showing a comparison of RIP14 and RIP15 sequences to other receptors. Percent sequence identities of RIP14 (panel A) and RIP15 (panel B) compared to DNA and ligand binding domains of the indicated receptor superfamily members are shown. For comparison, the isoform of each receptor member showing the highest score in a GenBank database search was used. TR: mouse thyroid hormone receptor α-1 (accession number: P16416); RAR: zebrafish retinoic acid receptor γ (accession number: LO3400); RXR: mouse retinoic acid X receptor α (accession number: P28700); EcR: *Drosophila* ecdysone receptor (accession number: P34021). Lengths of the various domains of the receptors are not to scale.

Figure 8A:
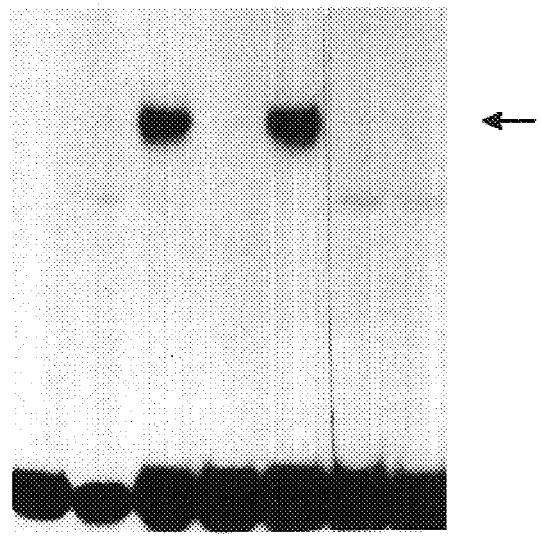
Figure 8B:
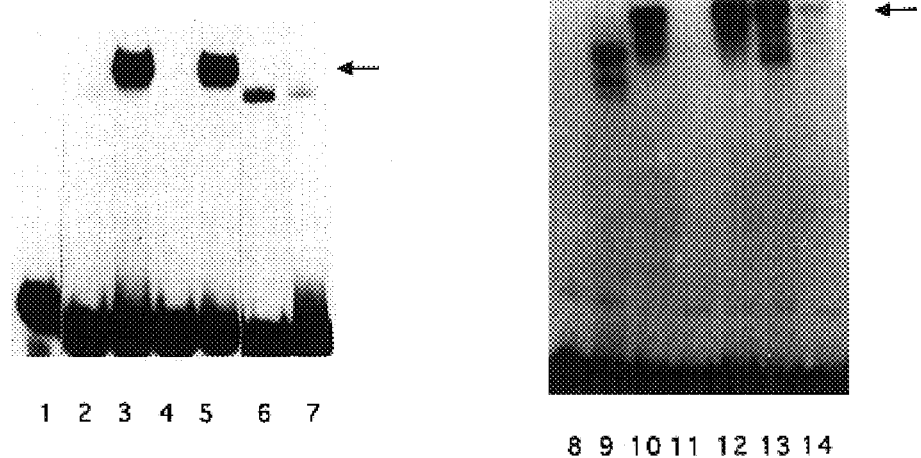

FIG. 8 is a series of photographs showing DNA binding by the RXR-interacting proteins. In panel A, RIP14-1 without (lane 2) or with RXR (lanes 3–5) was incubated with the hsp27 promoter (EcRE) end-labeled with [$^{32}$P]ATP. In panel B, RIP15 (lanes 2–5) and RIP14-1 (lanes 9–12) without (lanes 2 and 9) or with (lanes 3–5 and 10–12) RXR were incubated with βRARE end-labeled with [$^{32}$P]ATP. In both cases, a 50-fold molar excess of unlabeled specific (sp; EcRE, lane A4 and βRARE, lanes B4 and B11) or nonspecific (ns; AP1, lanes A5, B5, and B12) oligomers were added with the labeled probe. Incubations with probe alone are shown in lanes A1, B1, and B8. Cell lysates used for in vitro translation were also incubated with the probes without (lanes A6 and B6) or with (lanes A7 and B7) RXR. RIP14-2 and the RIP14-1 chimeras containing a four amino acid insertion in the D domain (RIP14C) were also incubated with βRARE and RXR as shown in lanes B13 and B14, respectively. Specific bands are indicated by arrows.

Figure 9:
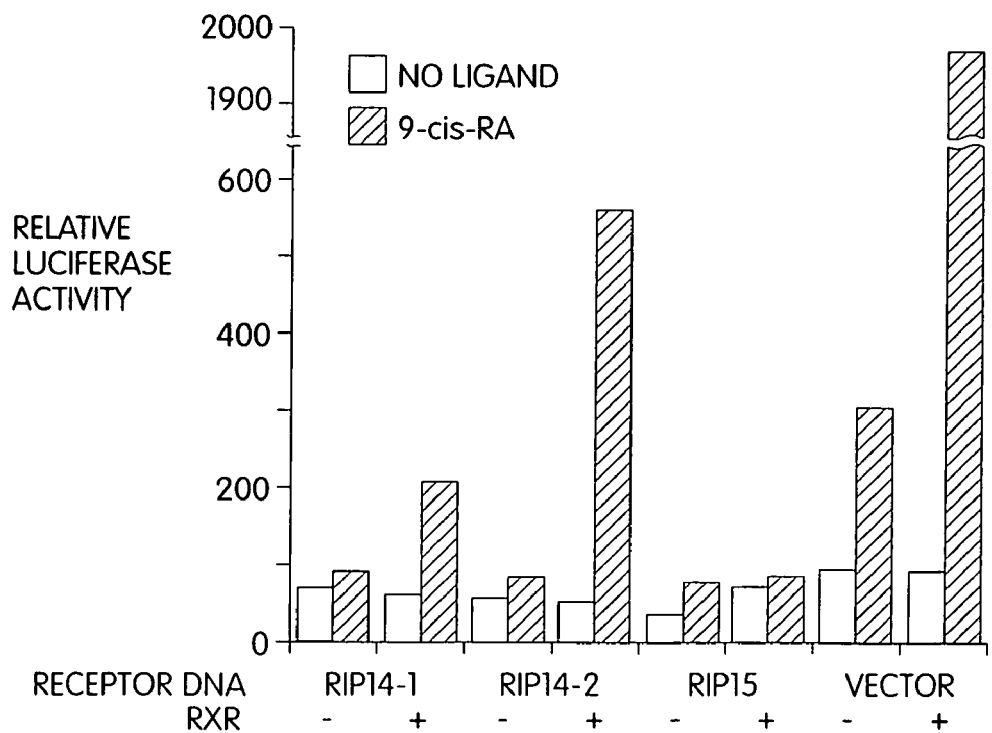

FIG. 9 is a graph showing activity of RIP14-1, RIP14-2, and RIP-15 in mammalian cells. Vectors expressing intact RIPs, RXR, or the CDM vector were cotransfected into HepG2 cells as indicated herein with a luciferase reporter plasmid containing three copies of the β-RARE and pTKGH as an internal control. 9-cis-RA was added at $10^{-6}$M approximately 18 hours after transfection. Results are luciferase expression normalized to the hGH internal control. Consistent results were obtained in three independent experiments.

FIG. 10 is the nucleotide (SEQ ID NO: 8) and deduced amino acid sequences (SEQ ID NO: 4) of RIP110.

FIG. 11 is the nucleotide (SEQ ID NO: 9) and deduced amino acid sequences (SEQ ID NO: 5) of RIP13.

DETAILED DESCRIPTION

Applicants have used an in vivo interaction trap system to identify and isolate proteins that physically interact with retinoid X receptors and, in particular, with the ligand binding domain of the human RXRα. These proteins are termed RXR-Interacting Proteins (or RIPs). The isolation and characterization of exemplary RIPs now follows.

Isolation of Proteins that Interact Specifically with RXR

Recently, several genetic methods have been used to identify and characterize protein—protein interactions (e.g., Fields et al., Nature 340:245–246, 1989; Gyuris et al., Cell 75:791–803, 1993). The principal idea of these systems is that transcription activation and DNA binding are quite distinct functions within most eukaryotic transcription activators, generally localized to two separate domains. Many functional examples of chimeric transcriptional activators consisting of the DNA binding domain of one protein attached to a heterologous activation domain have been characterized (Green et al., Nature 325:75–78, 1987; Ma et al., Cell 51:113–119, 1987). The fact that this attachment can be indirect, mediated by protein—protein interaction rather than the covalent linkage of separate domains of a single protein forms the basis of the selection. A version of this type of system, called the interaction trap, has allowed the isolation of several new proteins that interact with several different targets, including Max (Zervos et al., Cell 72:223–232, 1993), Cdc2 (Gyuris et al., Cell 75:791–803, 1993), and RAG-1 (Coumo et al., Proc. Natl. Acad. Sci. USA in press., 1994).

Figure 1:
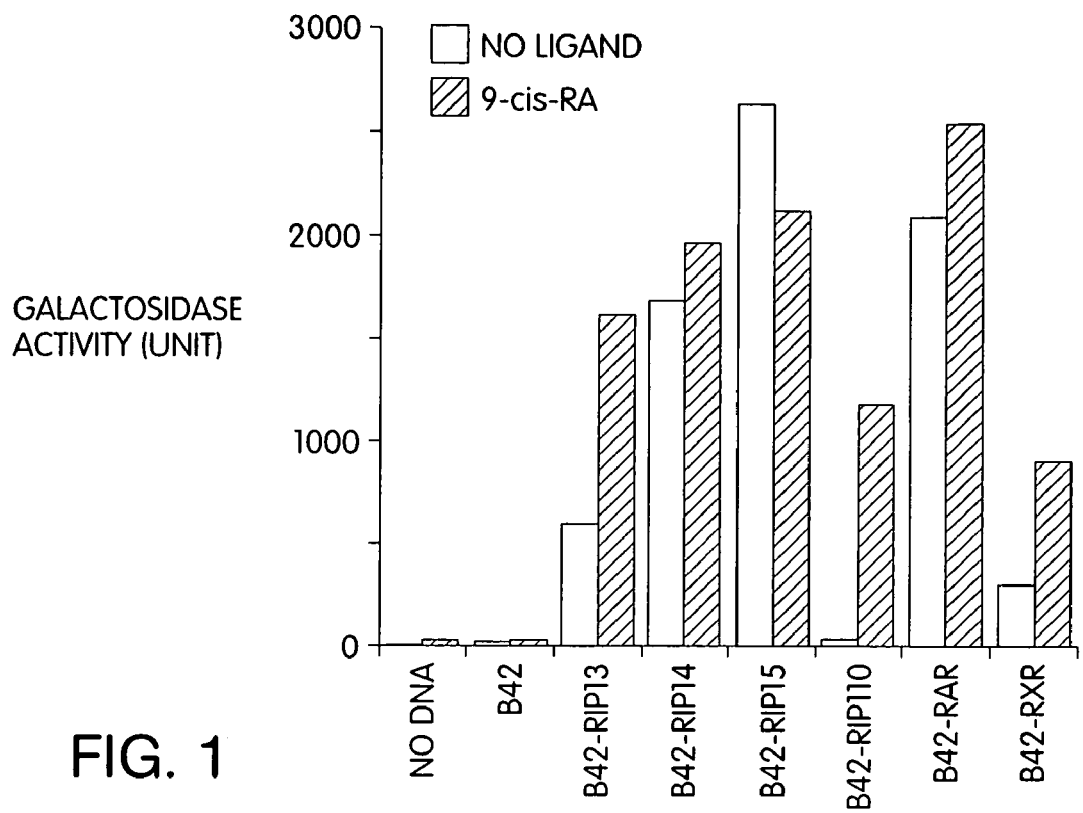
FIG. 1 is a graph showing βgalactosidase expression conferred to LexA-RXR by B42-RIP clones. A yeast strain containing a lacZ reporter gene under the control of LexA binding sites and LexA-RXR was transformed with the indicated B42-fusion protein expression vectors. Strains coexpressing LexA-RXR and the indicated B42 fusions were grown overnight in liquid in the presence or absence of $10^{-6}$M 9-cis-RA, added at the time of inoculation, and β-galactosidase activity was assayed.

We used the interaction trap (Gyuris et al., Cell 75:791–803, 1993) to identify cDNAs encoding proteins that interact with the ligand binding domain of human RXRα. As shown in FIG. 1, a chimeric protein consisting of the hinge (D) and ligand binding (E) domains of RXRα fused to the intact bacterial LexA repressor protein (LexA-RXR) is not a strong transcriptional activator in yeast, in either the presence or absence of 9-cis-RA. However, LexA-RXR does activate expression from LexA binding sites in cells which also express a fusion protein consisting of a transcriptional activation domain joined to another protein, such as the thyroid hormone receptor, which interacts specifically with RXR.

To isolate RXR-interacting proteins, we constructed a mouse liver cDNA library in a derivative of the yeast vector pJG4-5 (Gyuris et al., Cell 75:791–803, 1993; see below), in which the cDNA sequences are fused to the B42 transcriptional activation domain (Ma et al., Cell 51:113–119, 1987). The liver was chosen because it is a major target organ for the actions of a number of nuclear hormone receptor superfamily members. This library was introduced, as described herein, into a LexA-RXR expressing host in which transcription of both the β-galactosidase (β-gal) and LEU2 genes was under the control of LexA binding sites.

From $3\times10^6$ primary yeast transformants, a number of β-gal expressing colonies were identified in two independent screens carried out in the presence or absence of 9-cis-RA. Since expression of the B42-cDNA fusion proteins was induced by growth on galactose, candidates obtained from each condition were tested for galactose-dependent expression of both β-gal and LEU2, in the presence or absence of 9-cis-RA, using appropriate indicator plates (see below). To test the specificity of the interaction with RXR, cDNA plasmids were rescued from a number of candidates that showed appropriate galactose dependency and reintroduced into hosts expressing LexA alone or other LexA fusion proteins (e.g., LexA-Cdc2).

Candidates showing specific interaction with LexA-RXR were sequenced across the B42 fusion junction using an appropriate vector primer, and additional sequence was determined. The deduced amino acid sequences were compared to those in the GenBank and EMBL databases using the GCG (Devereux et al., Nucleic Acids Res. 12:387–395, 1984) and BLAST programs (Altschul et al., J. Mol. Biol. 215:403–410, 1990). This sequence comparison demonstrated that a number of the independently isolated clones encoded known RXR heterodimer partners, either PPAR (eight clones) or RARα (six clones), providing strong confirmation of the specificity of the screening. All of these clones included intact ligand binding domains, as expected from the fact that the major heterodimerization function lies within that domain. For PPAR (Issemann et al., Nature 347:645–650, 1990), three clones started at amino acid 84, just N-terminal to the DNA binding (C) domain, four others started at 91, within the C domain, and one at 170, just past the C domain. For RAR (Leroy et al., EMBO J. 10:59–69), all six clones started at amino acid 132, within the C domain. Although previous results demonstrated that LexA-RXR interacts strongly with a chimera consisting of B42 fused to the thyroid hormone receptor, no B42-TR clones were obtained, presumably as a consequence of the very low level of expression of the TR mRNAs in liver.

Six clones representing three independent B42 fusions to the vitamin D binding protein (Yang et al., Genomics 7:509–516, 1990) were isolated. Since this secretory protein is unlikely to interact with the nuclear RXR protein in intact cells, it is difficult to explain why these clones were obtained. It is possible that the vitamin D binding protein shares some structural similarity with the vitamin D receptor, which is an RXR heterodimer partner, and that this structural conservation is the basis for the interaction. However, it is also possible that the interaction of this protein with RXR is simply an artifact of the yeast system, and these clones have not been studied further.

Several additional clones encoded novel proteins. Two, RIP14 and RIP15, were previously undescribed orphan members of the nuclear receptor superfamily. As with the PPAR and RAR isolates, the B42 fusion junctions in both cases were near the beginning of the hinge (D) domain that separates the DNA (C) and ligand binding (E) domains. Two other clones, RIP13 and RIP110, showed no significant similarity to any known protein and are candidate transcriptional co-activators.

The level of β-gal expression conferred by several of the RXR interactors was examined more quantitatively (as described herein). The results of βgalactosidase assays of liquid cultures of a series of appropriate strains are shown in FIG. 1. As expected from previous results with B42-TR and numerous biochemical studies (Leid et al., Cell 68:377–395, 1992; Zhang et al., Nature 358:587–591, 1992), the interaction of B42-RAR with LexA-RXR was independent of the presence or absence of 9-cis-RA. Cells coexpressing LexA-RXR and the RIP14 and RIP15 chimeras showed levels of β-gal expression comparable to B42-RAR regardless of the presence or absence of the RXR ligand 9-cis-RA, indicating a relatively strong, ligand independent interaction with RXR. With RIP13, the significant β-gal expression observed in the absence of 9-cis-RA was increased approximately three fold in the presence of the ligand. For RIP110, only basal levels of expression were observed in the absence of 9-cis-RA, but the level of βgal expression was strongly induced in the presence of 9-cis-RA, indicating that the interaction of this protein with RXR is dependent on the presence of ligand.

Human cDNAs encoding any of these RIP polypeptides may be isolated using human cDNA libraries (for example, a human liver cDNA library) and standard techniques of hybridization.

Interaction of RIPs with Other Receptors

Interactions of the RIP clones with other superfamily members, including RAR, TR, the glucocorticoid receptor (GR), and MB67, an orphan isolated in this lab (Baes et al., Mol. Cell. Biol. 14:1544–1552, 1994) were also tested using a series of appropriate LexA fusions. In particular, the experiments shown in Table 1 were carried out as follows. Yeast transformants containing a lacZ reporter gene under the control of LexA binding sites and the indicated B42- and Lex-fusion protein expression vectors were transferred onto galactose-Ura⁻His⁻Trp⁻ plates containing X-gal and incubated for two days. Relative levels of β-galactosidase activity were estimated and are depicted as follows: B, blue (strong interaction); LB, light blue (weak interaction); W, white (no interaction); nt, not tested. At least three separate colonies were tested on the same plate for interaction. To test the effects of ligands, 100 µl of a $10^{-6}$M solution of the appropriate ligand was spread onto plates just before inoculation of cells (9-cis-RA for RXR, T3 for TR, and all-trans-RA for RAR). For B42-PPAR, the plasmid isolated from the screening was used. Both full length and truncated RAR fusions to LexA were tested with identical results for all the B42 fusions except B42-110, which was tested only with the full length fusion.

As indicated in Table 1, RIP13 and RIP110 interacted with all proteins except glucocorticoid receptor (GR), whereas RIP14 and RIP15 interacted with RXR only.

TABLE 1

| Lex Fusion | RXR | | TR | | RAR | | | |
|---|---|---|---|---|---|---|---|---|
| ligand | + | − | + | − | + | − | MB67 | GR |
| B42 fusion | | | | | | | | |
| 13 | B | B | B | B | B | B | B | W |
| 14 | B | B | W | W | W | W | W | W |
| 15 | B | B | W | W | W | W | W | W |
| 110 | B | LB | B | W | B | B | B | W |
| PPAR | B | B | W | W | nt | nt | nt | nt |
| RXR | B | B | B | B | B | B | B | W |

RIP13's interaction with all of the conventional receptors remained unaffected by the presence or absence of ligands. As with LexA-RXR, RIP110 interacted with LexA-TR in a ligand-dependent manner. Its interaction with LexA-RAR was not dependent on retinoic acid, however, and it also interacted constitutively with MB67, which does not have known ligands. This orphan showed substantial transcriptional activity in mammalian cells grown in the absence of any exogenously added ligands. The unique character of RIP13 and RIP110 in these interactions suggests that these proteins may have very important roles in conserved functions of the nuclear hormone receptor superfamily. In particular, the interaction of RIP13 with a wide array of superfamily members indicates that it may be involved in any of several processes that are common to a number of different receptors. In addition to direct transcriptional regulation, this could include nuclear transport, for example. The ligand-dependent nature of the interaction of RIP110 suggests that it may be directly involved in ligand-dependent transcription or other activities.

Isolation of Full-Length RIP14 and RIP15 cDNAs

Figure 2A:
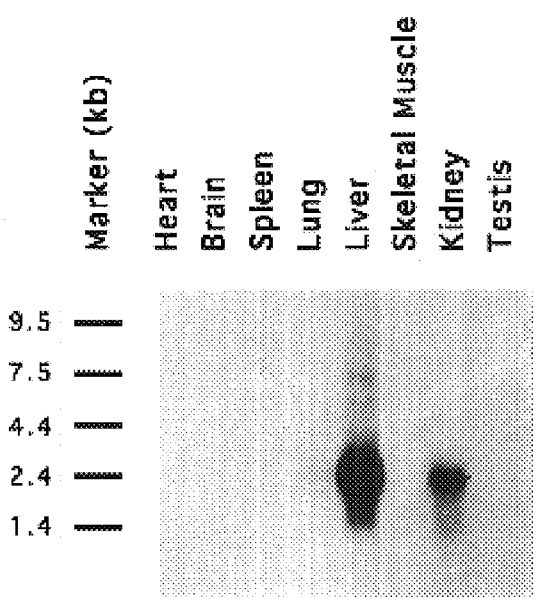
FIG. 2 is a Northern analysis of RIP14 (panel A) and RIP15 (panel B). A Northern blot containing mRNAs from the indicated tissues (Clontech, Palo Alto, Calif.) was hybridized with RIP14 and RIP15 probes. In a longer exposure of RIP14, several larger bands not evident in this exposure were observed in liver and kidney.
Figure 2B:
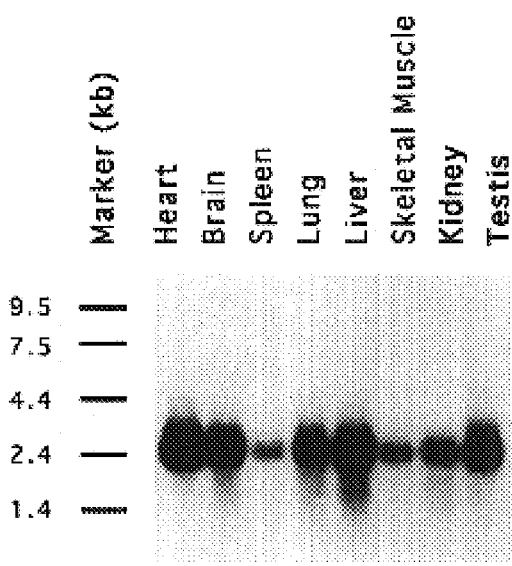

Northern blot analysis as described herein revealed that RIP14 is expressed only in liver and kidney in mouse, predominantly as a broad band of approximately 1.8 to 2.2 kb (FIG. 2). Much lesser amounts of three or four higher molecular weight species were also observed. In contrast, an approximately 2.3 kb RIP15 mRNA was universally expressed in a number of tissues. To obtain full-length clones of these mRNAs, a mouse liver cDNA library was constructed and screened by conventional hybridization with RIP14 and RIP15 probes. Eight separate clones were obtained for RIP14, and four for RIP15.

All eight RIP14 clones were analyzed by digestion with multiple restriction enzymes and either partial or complete sequencing. As diagrammed in FIG. 3, these clones may be divided into two subgroups that apparently encode distinct isoforms, referred to as RIP14-1 and RIP14-2. Based on initiation at the first methionine of the open reading frame, the RIP14-1 isoform is a protein of 484 amino acids. Since there are no in frame termination codons upstream from this methionine, it remains possible that this isoform includes additional N-terminal sequence. The RIP14-1 mRNA, however, is approximately 1.8 to 2.0 kb, as demonstrated by the hybridization of an oligonucleotide probe specific for the 5' end of the RIP14-1 sequence to only the lower portion of the broad band recognized by a common probe, and the cloned sequences account for approximately 2 kb, assuming a 200 nucleotide poly A tail. Thus, if such an N-terminal extension exists, it must be minimal. As many members of the receptor superfamily have 5' untranslated regions of several hundred nucleotides that include additional upstream AUG codons, it is also possible that the correct RIP14-1 sequence begins with a methionine downstream of that indicated in FIG. 4. For simplicity, we assume that the indicated reading frame is full length. As described below, results from in vitro translation are consistent with this assignment.

Figure 3:
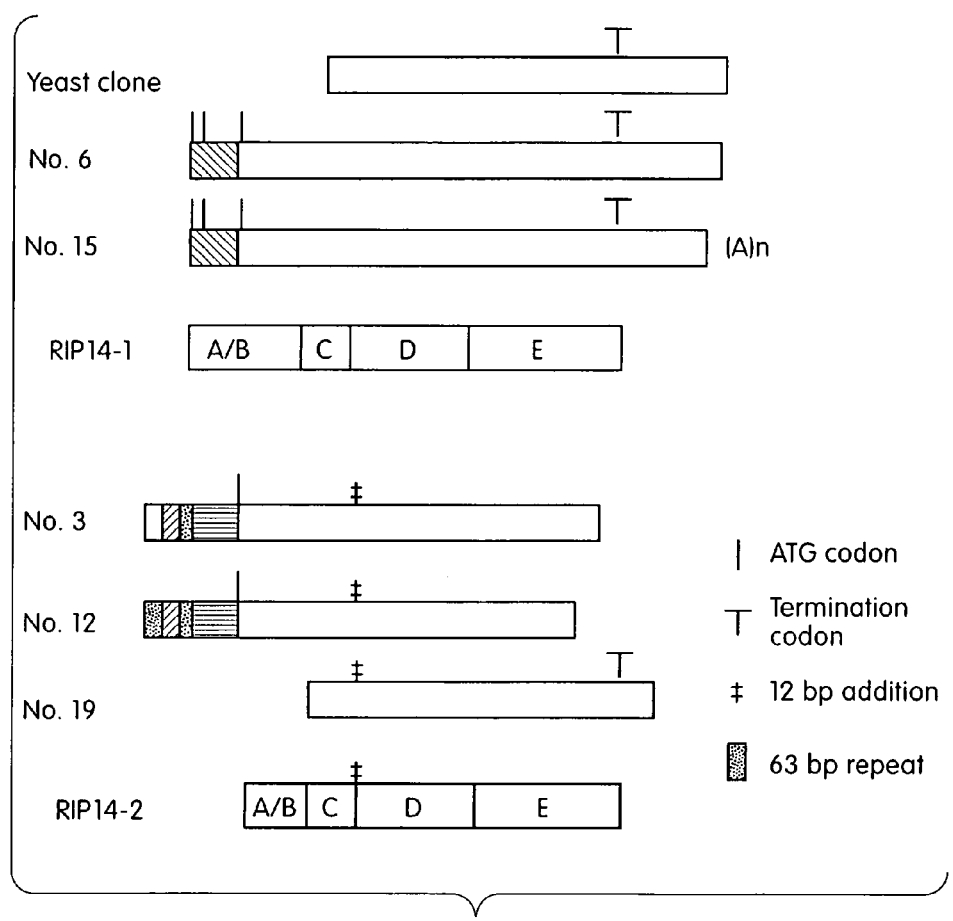
FIG. 3 is a schematic representation of the structure of the RIP14 cDNA and protein isoforms. The original yeast clone isolated from the interaction trap is diagrammed at the top. The positions of the putative initiation and termination codons are indicated, and the 12 base pair (bp) addition in the D domain of RIP14-2 is shown as ‡. Various sequences specific to each isoform and a 63 bp repeat present in Clone 12, but not Clone 3 are indicated.

The RIP14-2 group differed from RIP14-1 in two respects. First, Clones 3 and 12 shared related 5' sequences that diverged from those of RIP14-1 at a position within the apparent RIP14-1 coding region. Most of the 5' sequence specific to clone 12 consisted of an additional copy of a 63 base pair sequence from the region common to the RIP14-2 class (FIGS. 3 and 4). The basis for this variation is not known. As expected, hybridization with a probe specific for these more extensive RIP14-2 sequences detected the upper portion of the broad band recognized by the common probe, indicating that the full length RIP14-2 mRNA is approximately 2.0 to 2.2. kb. This corresponds well to the approximately 2.2 kb predicted from the sequence obtained, plus a poly A tail. Because of the divergent sequence, the first methionine of the open reading frame of the 451 amino acid RIP14-2 isoform corresponds to residue 38 of the predicted RIP14-1 sequence. RIP14-2 also differed from RIP14-1 by an insertion of four amino acids located four amino acids downstream of the C-terminus of the DNA binding domain. Although this insertion is only observed in clones that include the RIP14-2 type 5' end, it is possible that it is also present in a subset of mRNAs of the RIP14-1 type, and that it may be absent in a subset of mRNAs of the RIP14-2 type. However, there is currently no evidence for the existence of these two potential additional isoforms.

In contrast to the complex structure of RIP14, all of the clones of RIP15 show identical sequence, except one that is 64 base pairs longer at the 5' end. All four clones contain the same open reading frame for the predicted 446 amino acid RIP15 protein, with an in-frame terminator nine bases upstream of the initiation codon (FIG. 5).

In vitro translation of transcripts for the two RIP14 isoforms produced a slightly bigger protein for RIP14-1 than for RIP14-2, approximately 57 and 55 Kd (FIG. 6). This corresponds well to the predicted sizes of approximately 55 and 52 Kd, and is consistent with the assignment of the initiator codons. The calculated molecular weight of RIP15 is approximately 48 Kd. However, the major in vitro translation product was approximately 60 Kd (FIG. 6). The basis for this apparently aberrant migration is unclear.

In sum, therefore, the RIP15 gene apparently encodes a single product, while the RIP14 gene expresses at least two closely related isoforms. By analogy with several examples of alternate promoter utilization for other superfamily members, it seems likely that this mechanism accounts for the distinct 5' ends of the two major classes of RIP14 cDNAs. Because the cDNAs appear to be full length, the alternative possibility that they are derived by alternative splicing of a common transcript from a single promoter seems less likely. In contrast to this relatively common N-terminal variation, the variation of the RIP14 isoforms within the D domain is apparently unique within the receptor superfamily. Without information on the structure of the RIP14 gene, it is not possible to be certain how this variation is generated. However, since the first 6 nucleotides of the inserted sequence match the consensus 5' or donor splice site (GU (A/G)AGU) (SEQ ID NO: 10), it is quite likely that it is a consequence of alternative donor site utilization.

In FIG. 7, the amino acid sequences of the two orphans were compared to those of several other members of the nuclear hormone receptor superfamily. In the DNA binding (C) domain, RIP14 was most closely related to insect ecdysone receptors, sharing 82% sequence identity with that of *Drosophila* (Koelle et al., Cell 67:59–77, 1991), for example. Interestingly, RIP15 is the superfamily member next most closely related to RIP14 in this domain, with 67% identity. The DNA binding domains of RIP15 and the ecdysone receptors share 64% identity, and these three sequences form a rather divergent subgroup within the superfamily. A distinctive feature of the RIP15 C domain sequence is an insertion of two amino acids in the short region between the two zinc modules. Although they do not show particularly strong overall sequence identity with the RIP14/RIP15/ecdysone receptor subgroup elsewhere in the C domain, a similar insertion is present in the thyroid hormone receptors.

Both RIP14 and RIP15 included matches to all of the conserved sequence motifs present in the putative ligand binding and dimerization (E) domains of other orphans and conventional receptors (Seagraves et al., Genes & Dev. 4:204–219, 1990; Amero et al., Mol. Endocrinol 6:3–8, 1992; Laudet et al., EMBO J. 11:1003–1013, 1992), including a conserved C-terminal sequence associated with ligand dependent transcriptional activation (Danielian et al., EMBO J. 11:1025–1033, 1992). As with the C domain, overall comparisons based on ligand/dimerization domains placed both RIP14 and RIP15 in a divergent subgroup that also includes the ecdysone receptors. Within this region, RIP14 shares 42% and 37% identity with RIP15 and the ecdysone receptor, respectively, while RIP15 shares 42% identity with the ecdysone receptor. Overall, these three proteins are approximately as closely related to each other as the TRs are to the RARs.

Heterodimers of RIP14 and RIP15 with RXR Bind DNA Specifically

To identify DNA sequences recognized by each orphan, in vitro translated proteins were used for gel shift assays. Because of their strong sequence similarity to the ecdysone receptor, a well studied ecdysone response element (EcRE) from the *Drosophila* hsp27 promoter (Riddilough et al., EMBO J. 6:3729–3734, 1987) was tested for binding to both orphans, in the presence and absence of RXR. This element consists of two hexamers that match the receptor binding consensus AGGTCA, arranged as an inverted repeat separated by one base pair (IR-1). As demonstrated in FIG. 8, panel A, RIP14-1 bound to the EcRE, but only in the presence of RXR. The binding of the RIP14-2 isoform to this element was weaker than that of RIP14-1 when similar amounts of RIP14 proteins were used. RIP15 did not bind to the EcRE regardless of the presence or absence of RXR. Several other DNA elements were tested in the gel shift assay, including the retinoic acid response element from the promoter of the human RARβ2 isoform (βRARE) (de The et al., Nature 343:177–180, 1990). In the presence of RXR, the βRARE was bound by both the RIP14 isoforms and RIP15 (FIG. 8, panel B). Again, the binding of the RIP14-2/RXR heterodimer was weaker than the RIP14-1/RXR heterodimer when a similar amount of RIP14 proteins were used (FIG. 8, panel B, lanes 10 and 14). In contrast to the results with the EcRE, RIP14-1 showed some binding to the βRARE in the absence of RXR.

The difference in apparent binding affinity between RIP14-1 and RIP14-2 could be due to either the variation in the short A/B domains or the four additional amino acids in the D domain of RIP14-2. The former would be consistent with the recently reported effects of different A/B domains on DNA binding by isoforms of the orphan ROR (Giguere et al., Genes & Dev. 8:538–553, 1994). The latter would be consistent with the fact that the insertion occurs within a region called the T box (Wilson et al., Science 2546: 107–110, 1992), which is associated with effects on DNA binding to direct repeats by heterodimers of other superfamily members. A chimeric receptor containing the four additional amino acids (MYTG) of RIP14-2 at the corresponding region of the D domain of RIP14-1 was constructed and tested for binding to both the βRARE and EcRE in the presence of RXR. As shown in FIG. 8, panel B, lane 13, the binding of this chimeric protein (RIP14C) to the βRARE was similar to that of isoform 1 rather than isoform 2. The EcRE also showed a similar result. The lack of an effect of the insertion on RIP14-1 binding suggests that the differences in the A/B domain may determine relative binding affinity of the two isoforms.

From the above results, we conclude that both RIP14 and RIP15 bind to an overlapping set of specific elements as heterodimers with RXR.

The at least partially overlapping DNA binding specificity of RIP14 and RIP15 is consistent with the similarity of their DNA binding domains and suggests that they may have overlapping functional roles. Since both interact with the βRARE, it is possible that these functions include effects on the complex response to retinoids. However, the inactivity of both intact and chimeric versions of the two orphans in transient transfections indicates that both require activation by binding of as yet unidentified ligands or by other processes.

Function of RIP14 and RIP15 In Vivo

To test the transcriptional activity of RIP14-1, RIP14-2, and RIP15, vectors expressing each were cotransfected into HepG2 cells with a luciferase reporter plasmid in which three copies of the βRARE were inserted upstream of the TK promoter (Baes et al., Mol. Cell. Biol. 14:1544–1552, 1994; described herein). Expression from this reporter was transactivated more than 100 fold by RAR in the presence of retinoic acid, and 20–50 fold by the apparently constitutive orphan MB67 (Baes et al., Mol. Cell. Biol. 14:1544–1552, 1994). Neither of the two RIP14 isoforms or RIP15 was able to transactivate the βRARE reporter under any condition tested (FIG. 9). This was confirmed using chimeras in which the A/B and DNA binding (C) domains of the thyroid hormone receptor (TR) were fused to the hinge (D) and ligand binding (E) domain of each orphan. In cotransfections of these chimeras with an analogous reporter plasmid containing two copies of the synthetic palindromic T3 response element (TREpal) (Brent et al., Mol. Endocrinol. 3:1996–2004, 1989), the TR-RIP14 chimera was not significantly different from the CDM vector alone. A two to three fold activation was observed with the TR-RIP15 chimera under a variety of conditions. However, this effect was quite modest by comparison to the more than 50 fold activation observed with TR in the presence of T3.

These transfection data suggest that both orphans may need specific ligands to activate transcription. A number of compounds considered potential ligands for orphan receptors were tested, including several hydroxycholesterols, dehydroepiandrosterone (DHEA), α-tocopherol, thyroid hormone (T3), reverse T3, and several retinoids. No specific activity was observed with any of these compounds.

In cotransfections of the orphans with RXRα, basal expression was unaffected (FIG. 9). In the presence of 9-cis-RA, cotransfection with RXR alone resulted in strong activation of the βRARE reporter (FIG. 9). Previous results (Zhang et al., Nature 358:587–591, 1992) suggested that this effect was largely mediated by RXR homodimers, although heterodimers of RXR with endogenous RARs could also contribute. Cotransfection with RIP14-1 decreased 9-cis-RA induced expression by approximately 90%, and contransfection with RIP15 blocked it completely (FIG. 9). RIP14-2, which bound βRARE with somewhat lower apparent affinity, decreased the level of 9-cis-RA induced expression by 60% (FIG. 9). These inhibitory effects could be due either to direct binding of inactive RIP/RXR heterodimers to βRARE, or to indirect effects of sequestration of RXR in complexes. In either case, the results confirmed that RIP proteins were expressed in such transfections and suggested that both orphans may be involved in the complex retinoid response.

RIP110 and RIP13

RIP110 and RIP13 cDNAs were sequenced by standard techniques and deduced amino acid sequences determined, also by standard techniques. These sequences are presented in FIGS. 10 and 11.

The materials and methods used in the above experiments are now described.

Strains and Plasmids

LexA fusion proteins were expressed from derivatives of the LexA fusion vector (LexA(1-202)+PL) (Gyuris et al., Cell 75:791–803, 1993), which expresses the intact LexA protein. The LexA-RXR and LexA-TR fusions included human RXRα and rat TRβ sequences extending from the C-terminal portion of the DNA binding domain to the C-terminus. Analogous LexA fusions to RAR, MB67, and GR were constructed using PCR (polymerase chain reaction). For LexA-RAR, an additional fusion to the intact RARα was also generated. B42 fusion proteins were either isolated from the cDNA library as described below or inserted into a derivative of the vector pJG4-5 (Gyuris et al., Cell 75:791–803, 1993) using standard procedures. For in vitro translation, appropriate fragments were cloned into a previously described bacteriophage T7 promoter expression vector (Carter et al., Mol. Cell. Biol. in press., 1994) and expressed using bacteriophage T7 RNA polymerase. Mammalian expression vectors were derivatives of CDM (Seed, Nature 329:840–842, 1987), and reporter plasmids were derivatives of pTKluc (Carter et al., Mol. Cell. Biol. in press, 1994) in which the herpes virus TK promoter directs expression of luciferase.

Yeast strains were derivatives of EGY48 (MATα leu2 trp1 ura3 his3 LEU2::pLexop6-LEU2 (ΔUAS LEU2)) (Gyuris et al., Cell 75:791–803, 1993; Zervos et al., Cell 72:223–232, 1993), in which expression of the chromosomal LEU2 gene is under the control of LexA operators. EGY48 was successively transformed with 8H18-34 (Gyuris et al., Cell 75:791–803, 1993), in which expression of the E. coli lacZ (β-galactosidase) gene is also under the control of lexA operators (selection for URA3$^+$), and derivatives of the LexA fusion expression vector LexA(1-202)+PL (Gyuris et al., Cell 75:791–803, 1993) (selection for HIS3$^+$).

cDNA Library Screening and Characterization of RXR Interactors

An oligo(dT)-primed mouse liver cDNA library was constructed using standard procedures (Ausubel et al., Current Protocols in Molecular Biology, Greene Pub. Assoc. New York, 1994) in the plasmid cgatrp2 (selection for TRP1$^+$), a derivative of the B42 expression vector pJG4-5. This plasmid also contains a tRNA suppressor gene, supF, which can be used to rescue only cgatrp2 (and not the other two plasmids present in the yeast host) after transformation to an Escherichia coli strain containing a P3 plasmid. The library was amplified and used to transform an EGY48 derivative expressing LexA-RXR. 3×10$^6$ primary yeast transformants were obtained from glucose-Ura$^-$His$^-$Trp$^-$ plates and recovered as described (Gyuris et al., Cell 75:791–803, 1993). 2×10$^7$ of these cells were plated on galactose-Ura$^-$His$^-$Trp$^-$Leu$^-$ plates with or without 9-cis-RA. About 100 LEU2 expressing colonies were selected for X-gal testing on galactose-Ura$^-$His$^-$Trp plates. Forty were chosen for further analysis based on stable galactose dependency of both growth on Leu$^-$ plates and expression of β-galactosidase (Gyuris et al., Cell 75:791–803, 1993; Zervos et al., Cell 72:223–232, 1993). The cDNA plasmids were recovered by transformation of E. coli MC1063/P3 and reintroduced into host strains expressing LexA-RXR, LexA alone, or other chimeras such as LexA-Cdc2 (Gyuris et al., Cell 75:791–803, 1993) to test specificity of the interaction. Candidates that interacted specifically with LexA-RXR were selected and sequenced with a primer from the fusion site of the B42 transcription domain by the standard dideoxynucleotide method. Based on sequence information and pattern of restriction endonuclease digestion, candidate clones were divided into several classes. In some cases, further sequence information was obtained. The obtained sequences were used to search sequence databases. To isolate clones containing the full length RIP14 and RIP15 cDNAs, a mouse liver cDNA library constructed in the CDM8 plasmid by standard procedures was screened by conventional hybridization methods with fragments of RIP14 and RIP15 which were [$^{32}$P]-labeled by random priming.

β-Galactosidase Assay of RXR-Interacting Clones

An EGY48 derivative containing the 8H18-34 lacZ reporter plasmid was successively transformed with LexA and B42-fusion protein expression vectors to generate a series of strains coexpressing each LexA fusion with each B42 fusion. At least two separate colonies from glucose-Ura$^-$His$^-$Trp$^-$ plates were selected randomly for each coexpressing strain and used to inoculate galactose-Ura$^-$His$^-$Trp$^-$ liquid media to induce expression of the B42 fusion protein (Gyuris et al., Cell 75:791–803, 1993). Cultures were assayed for β-galactosidase as described (Ausubel et al., Current Protocols in Molecular Biology, Greene Pub. Assoc., New York, 1994).

RNA Analysis

A Northern blot containing 2 μg of polyA$^+$ mRNA from the indicated tissues (Clontech, Inc., Palo Alto, Calif.) was hybridized with probes labeled by random priming using standard procedures (Ausubel et al., Current Protocols in Molecular Biology Greene Pub. Assoc., New York, 1994).

Cell Culture and Transfections

HepG2 cells were propagated in Dulbecco's modified Eagle's medium containing 10% fetal bovine serum. Transfections were carried out using calcium phosphate precipitation in the same medium, or in medium supplemented with charcoal stripped serum, as described (Baes et al., Mol. Cell. Biol. 14:1544–1552, 1994). HepG2 cells plated on six well culture plates were cotransfected with 1 μg of plasmids expressing intact RIPs, with or without 0.25 μg of RXRα vector, and with 1.5 μg of a reporter plasmid containing three copies of the βRARE (Baes et al., Mol. Cell. Biol. 14:1544–1552, 1994), and 2 μg of pTKGH as an internal control. Luciferase activity was normalized using the level of growth hormone expressed from pTKGH. Each transfection was done in duplicate.

Proteins and Gel Shift Assay

RIP14 and RIP15 proteins were produced by in vitro translation (Promega TNT, Madison, Wis.) using expression vectors containing the RIP genes following a T7 promoter. To generate full length RIP14-2 constructs, fragments from RIP14-1 clone No. 15 containing regions from the middle of the E domain to the 3' end replaced the corresponding regions of RIP14-2 Clones No. 3 or 12, respectively. Sequences were confirmed by DNA sequencing. Human RXRα protein was expressed in E. coli using a bacterial expression vector based on the bacteriophage T7 promoter (Carter et al., Mol. Cell. Biol. in press., 1994). The oligonucleotides used for gel shift assays were as following: β-RARE, 5' gatccgggtagGGTTCAccgaaAGTTCActcga 3' (SEQ ID NO: 11); hsp27, 5' ctagacaagGGTTCAaTGCACTtgtccatcg 3' (SEQ ID NO: 12). Hexamers that match the AGGTCA (SEQ ID NO: 13) consensus half site or its complement are capitalized. Double stranded oligonucleotides were end-labeled using [$^{32}$P]ATP and kinase, and free nucleotide was removed by gel filtration. Proteins were preincubated with 20 μl of gel shift assay buffer (10 mM Tris (pH 8.0), 40 mM KCl, 0.05% NP-40, 10% glycerol, 1 mM DTT, 2.5 mM MgCl$_2$ and 5 ng of poly dI-dC) for 10 minutes in ice. This mixture was then combined with the indicated labeled probe and incubated for 20 minutes at room temperature. Specific or nonspecific competitor oligomers were added with the probe. The mixtures were analyzed by 6% non-denaturing polyacrylamide gel electrophoresis using 0.5×Tris-Borate-EDTA (TBE) buffer at 4° C.

Identification of Ligands which Bind RXR-Interacting Proteins

Isolation of cDNAs encoding RXR-interacting proteins enables the identification and isolation of their ligands. Accordingly, one aspect of the invention features a screening assay for the identification of compounds which specifically bind to the RXR-interacting proteins described herein. Such an assay may be carried out using a recombinant RXR-interacting protein.

In one example, the RXR-interacting protein component is produced by a cell that naturally produces substantially none of the protein or by a cell which produces functionally deficient protein; suitable cells are, e.g., those discussed above with respect to the production of recombinant receptor, most preferably, mammalian cells such as HepG2 cells. Host cells are transfected with (1) a vector which expresses a nucleic acid encoding the RXR-interacting protein (i.e., the "producer vector") and (2) a vector which includes an RXR-interacting protein binding site (e.g., for RIP14 and RIP15, the βRARE sequence described herein) positioned upstream of a target gene which may be assayed (e.g., a CAT gene, a luciferase gene, or a β-galactosidase gene) (i.e., the "reporter vector"). Using a standard transactivation assay procedure (for example, the assay described herein), RXR-interacting protein activity is assayed by measuring binding site-dependent target gene expression. Useful ligands are identified as those compounds which, when added to the host cell medium, effect a change in RXR-interacting protein-directed gene expression (as detected using any reporter vector); useful ligands according to the invention may either increase or decrease RXR-interacting protein activity.

Any suitable transactivation technique, producer vector, and binding site-containing reporter vector may be used. Descriptions of transactivation assays and generally useful vectors for the identification of ligands which bind other nuclear hormone receptors are described, e.g., in Evans et al. (U.S. Pat. No. 4,981,784, 1991); Evans et al. (WO 90/07517); Evans et al. (WO90/01428); and WO88/03168; all hereby incorporated by reference. RXR-interacting proteins which may be used to screen for ligands include wild-type molecules as well as any appropriate chimeric protein, for example, those chimeric proteins described herein.

Candidate ligands may be purified (or substantially purified) molecules or the ligand may be one component of a mixture of ligands (e.g., an extract or supernatant obtained from cells; Ausubel et al., supra). In a mixed ligand assay, the RXR-interacting protein ligand is identified by testing progressively smaller subsets of the ligand pool (e.g., produced by standard purification techniques, e.g., HPLC or FPLC) until a single ligand is finally demonstrated to modulate the protein's activity. Candidate ligands include peptide as well as non-peptide molecules.

Alternatively, a ligand may be identified by its ability to bind an RXR-interacting protein using affinity chromatography. Recombinant protein is purified by standard techniques, from cells engineered to express the protein (e.g., those described above); the recombinant protein immobilized on a column (e.g., a Sepharose column or a streptavidin-agarose column by the immunoaffinity method of Ausubel et al., supra) and a solution containing one or more candidate ligands is passed through the column. Such a solution (i.e., such a source of candidate ligands) may be, e.g., a cell extract, mammalian serum, or growth medium on which mammalian cells have been cultured and into which the cells have secreted factors (e.g., growth factors) during culture; again, candidate ligands include peptide as well as non-peptide molecules. A ligand specific for a recombinant RXR-interacting protein is immobilized on the column (because of its interaction with the protein). To isolate the ligand, the column is first washed to remove non-specifically bound molecules, and the ligand of interest is then released from the column and collected.

Ligands isolated by the above methods (or any other appropriate method) may, if desired, be further purified (e.g., by high performance liquid chromatography; see above). Once isolated in sufficiently-purified form, a novel peptide ligand may be partially sequenced (by standard amino acid sequencing techniques). From this partial amino acid sequence, a partial nucleic acid sequence is deduced which allows the preparation of primers for PCR cloning of the ligand gene (e.g., by the method of Ausubel et al., supra).

Identification of RXR-Interacting Protein DNA Binding Sites

Identification of the RXR-interacting proteins facilitates identification of their DNA binding sites. According to one approach, DNA binding sites may be identified using a gel shift assay, e.g., as described above for the identification of the RIP14 and RIP15 binding sites. Alternatively, a transactivation assay may be utilized. Briefly, candidate DNA binding sites are inserted upstream of a target gene whose expression may be assayed and the ability of an RXR-interacting protein to bind the DNA site is assayed as its ability to activate downstream gene expression.

Alternatively, a DNA binding site may be identified by selectively retaining a protein-bound DNA fragment on a nitrocellulose filter. This approach relies on the ability of nitrocellulose to bind proteins but not double-stranded DNA. Purified RXR-interacting protein (e.g., purified by standard techniques from cells engineered to express the protein, e.g., those described above) is mixed with labelled double-stranded DNA (e.g., a random pool of DNA fragments) under conditions which allow interaction. After incubation, the mixture is suction-filtered through nitrocellulose, allowing unbound DNA to pass through the filter while retaining the protein and any DNA specifically bound to it. Bound DNA fragments are then eluted from the filter and analyzed by gel electrophoresis or amplification and cloning. A detailed description of this technique is published in Ausubel et al. (supra).

Candidate DNA fragments for either approach may be derived, for example, from a randomly cleaved or sonicated genomic DNA library, a randomly generated set of oligonucleotides, and/or may be derived from known nuclear hormone response elements (see, e.g., Evans et al., WO90/11273).

Identification of RXR-interacting protein DNA binding sites facilitates a search for the presence of such sites upstream of known or yet unidentified genes (e.g., by an examination of sequences upstream of known genes or by standard hybridization screening of a genomic library with binding site probes). RXR-interacting protein-mediated transcriptional control of genes bearing the binding site upstream may then be investigated (e.g., by transactivation experiments as described above), potentially leading to the elucidation of novel RXR-interacting protein functions.

Chimeric Receptors

The functional domains of the RXR-interacting proteins may be swapped with the domains of other members of the nuclear hormone receptor family (see, e.g., Evans et al., WO 90/11273; Evans, *Science* 240:889, 1988) in order to produce receptors having novel properties. For example, fusion of an RXR-interacting protein DNA binding domain to the ligand-binding and gene activation domains of glucocorticoid receptor would confer hormonal regulation on genes downstream of RIP binding sites. Alternatively, fusion of an RXR-interacting protein DNA binding domain to a trans-repressing domain (see, e.g., Evans et al., WO90/14356) would result in repression of the basal level of expression of genes bearing upstream RIP binding sites. Examples of receptor domains which may be included in a chimeric RIP receptor are described in Evans et al. (WO 90/15815) and in Evans et al. (*Science* 240:889, 1988). Construction of receptor fusion genes is carried out by standard techniques of molecular biology.

Dominant Negative Mutants

Mutants of RXR-interacting proteins may be generated which interfere with normal RIP activity. Such mutants are termed "dominant negative" and fall into at least two classes: (a) ones which bind to their DNA binding site (thereby interfering with the ability of wild-type RXR-interacting protein to bind the same site) but which do not activate ligand-dependent gene expression and (b) ones which heterodimerize with other receptors (e.g., RXR) but which do not promote the biological response associated with the wild-type heterodimer.

The first class of RIP dominant negative mutants include those receptor polypeptides which contain a wild-type DNA binding domain and a mutant gene activation domain. Such mutants are unable to transactivate a reporter gene even in the presence of ligand (e.g., as measured using a CAT reporter gene with an upstream βRARE and the standard methods described above) but retain the ability to bind a RIP DNA binding site (as evidenced, e.g., by DNA footprint analysis using a βRARE DNA sequence; Ausubel et al., supra).

The second class of RIP dominant negative mutants include those receptor polypeptides which contain a wild-type heterodimerization domain. Such a mutant interacts with its heterodimer partner and disrupts the partner's function. In one particular example, a dominant negative RIP-interacting protein may be overproduced (e.g., by directing its expression from a very strong promoter); the abundant protein forms heterodimers with cellular RXR protein, soaking up available RXR and thereby preventing RXR homodimer formation as well as RXR heterodimer formation with other partner proteins (e.g., RAR, VDR, and T3R). Wild-type RXR-interacting protein may function as a dominant negative mutant if overproduced in this manner. However, a mutant RXR-interacting protein lacking gene activation function and/or a DNA binding domain is preferred.

Any of the above mutants may be generated by any method of random or site-directed DNA mutagenesis (see, e.g., Ausubel et al., supra).

Identification of Molecules that Modulate RXR-Interacting Protein Receptor Expression Isolation of genes encoding RXR-interacting proteins also facilitates the identification of molecules which increase or decrease RIP expression. According to one approach, candidate molecules (e.g., peptide or non-peptide molecules found, e.g., in a cell extract, mammalian serum, or growth medium on which mammalian cells have been cultured) are added at varying concentrations to the culture medium of cells which express RIP mRNA. RIP expression is then measured by standard Northern blot analysis (Ausubel et al., supra) using RIP cDNA as a hybridization probe. The level of RIP expression in the presence of the candidate molecule is compared to the level measured for the same cells in the same culture medium but in the absence of the candidate molecule. A molecule which promotes an increase or decrease in RIP expression is considered useful in the invention.

RXR-Interacting Protein Expression

In general, RXR-interacting proteins according to the invention may be produced by transformation of a suitable host cell with all or part of an RXR-interacting protein-encoding cDNA fragment (e.g., the cDNA described above) in a suitable expression vehicle.

Those skilled in the field of molecular biology will understand that any of a wide variety of expression systems may be used to provide the recombinant protein. The precise host cell used is not critical to the invention. The RXR-interacting protein may be produced in a prokaryotic host (e.g., *E. coli*) or in a eukaryotic host (e.g., *Saccharomyces cerevisiae* or mammalian cells, e.g., COS 1, NIH 3T3, or HeLa cells). Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The method of transformation or transfection and the choice of expression vehicle will depend on the host system selected. Transformation and transfection methods are described, e.g., in Ausubel et al. (*Current Protocols in Molecular Biology*, John Wiley & Sons, New York, 1994); expression vehicles may be chosen from those provided, e.g., in *Cloning Vectors*: A Laboratory Manual (P. H. Pouwels et al., 1985, Supp. 1987).

One preferred expression system is the mouse 3T3 fibroblast host cell transfected with a pMAMneo expression vector (Clontech, Palo Alto, Calif.). pMAMneo provides: an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding an RXR-interacting protein would be inserted into the pMAMneo vector in an orientation designed to allow expression. The recombinant RXR-interacting protein would be isolated as described below. Other preferable host cells which may be used in conjunction with the pMAMneo expression vehicle include COS cells and CHO cells (ATCC Accession Nos. CRL 1650 and CCL 61, respectively).

Alternatively, an RXR-interacting protein is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the RXR-interacting protein is cloned into an expression vector which includes the dihydrofolate reductase (DHFR) gene. Integration of the plasmid and, therefore, the RXR-interacting protein-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR-cells, ATCC Accession No. CRL 9096) are among the host cells preferred for DHFR selection of a stably-transfected cell line or DHFR-mediated gene amplification.

Once the recombinant RXR-interacting protein is expressed, it is isolated, e.g., using affinity chromatography. In one example, an anti-RXR-interacting protein antibody (e.g., produced as described herein) may be attached to a column and used to isolate the RXR-interacting protein. Lysis and fractionation of RXR-interacting protein-harboring cells prior to affinity chromatography may be performed by standard methods (see, e.g., Ausubel et al., supra). Alternatively, an RXR-interacting protein fusion protein, for example, an RXR-interacting protein-maltose binding protein, an RXR-interacting protein-βgalactosidase, or an RXR-interacting protein-trpE fusion protein, may be constructed and used for RXR-interacting protein isolation (see, e.g., Ausubel et al., supra; New England Biolabs, Beverly, Mass.).

Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short RXR-interacting protein fragments, can also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification can also be used to produce and isolate useful RXR-interacting protein fragments or analogs (described herein).

Anti-RXR-Interacting Protein Antibodies

Human RXR-interacting proteins (or immunogenic fragments or analogues) may be used to raise antibodies useful in the invention; such polypeptides may be produced by recombinant or peptide synthetic techniques (see, e.g., *Solid Phase Peptide Synthesis*, supra; Ausubel et al., supra). The peptides may be coupled to a carrier protein, such as KLH as described in Ausubel et al., supra. The KLH-peptide is mixed with Freund's adjuvant and injected into guinea pigs, rats, or preferably rabbits. Antibodies may be purified by peptide antigen affinity chromatography.

Monoclonal antibodies may also be prepared using the RXR-interacting proteins described above and standard hybridoma technology (see, e.g., Kohler et al., Nature 256: 495, 1975; Kohler et al., *Eur. J. Immunol.* 6:511, 1976; Kohler et al., *Eur. J. Immunol.* 6:292, 1976; Hammerling et al., *In Monoclonal Antibodies and T Cell Hybridomas*, Elsevier, N.Y., 1981; Ausubel et al., supra).

Once produced, polyclonal or monoclonal antibodies are tested for specific RXR-interacting protein recognition by Western blot or immunoprecipitation analysis (by the methods described in Ausubel et al., supra). Antibodies which specifically recognize an RXR-interacting protein are considered to be useful in the invention; such antibodies may be used, e.g., in an immunoassay to monitor the level of RXR-interacting protein produced by a mammal (for example, to determine the subcellular location of any of these retinoid X receptor interacting proteins.

Preferably, antibodies of the invention are produced using fragments of the RXR-interacting protein which lie outside highly conserved regions and appear likely to be antigenic, by criteria such as high frequency of charged residues. In one specific example, such fragments are generated by standard techniques of PCR and cloned into the pGEX expression vector (Ausubel et al., supra). Fusion proteins are expressed in *E. coli* and purified using a glutathione agarose affinity matrix as described in Ausubel, et al., supra). *Current Protocols in Molecular Biology* (Greene Pub. Assoc., New York, 1994)). To attempt to minimize the potential problems of low affinity or specificity of antisera, two or three such fusions are generated for each protein, and each fusion is injected into at least two rabbits. Antisera are raised by injections in a series, preferably including at least three booster injections.

Antisera is cleared of anti-GST antibodies using GST immobilized on a glutathione column, and the antisera are checked by ELISA for titer and specificity, using GST fusion proteins as controls. Antisera is also checked for its ability to immunoprecipitate in vitro translated RXR-interacting proteins or control proteins, such as glucocorticoid receptor, CAT, or luciferase. Western blots of total or nuclear versus cytoplasmic fractionated HeLa cell proteins are also probed with the antisera to assess specificity and to characterize subcellular compartmentalization. In these and other immunologic assays, specificity is confirmed by the specific competition with the GST fusion protein.

Once the specificity of an antiserum is confirmed, it may be used in any standard indirect immunofluorescence procedure to determine the subcellular distribution of the RXR-interacting protein in a particular cell type.

Use

The proteins described herein interact with retinoid X receptor and are thus likely to mediate or modulate RXR function. In particular examples, RIP14 and RIP15 block RXR-dependent activation of β-RARE linked genes, and such proteins (or peptides derived from these proteins, particularly, short peptides which are capable of RXR interaction), may facilitate the production of pharmacologic modifiers of RXR function. Such therapeutic polypeptides of the invention may be administered by any appropriate route, e.g., intravenously, at a dosage which is effective to modulate RXR function. Treatment may be repeated as necessary for alleviation of disease symptoms.

The polypeptides of the invention are also useful for identifying those compartments of mammalian cells which contain proteins important to the function of the retinoid X receptor. Antibodies specific for a particular RXR-interacting protein may be produced as described above. The normal subcellular location of the protein is then determined either in situ or using fractionated cells by any standard immunological or immunohistochemical procedure (see, e.g., Ausubel et al., supra; Bancroft and Stevens, *Theory and Practice of Histological Techniques*, Churchill Livingstone, 1982).

Antibodies specific for RXR-interacting proteins also find diagnostic use in the detection or monitoring of RXR-related diseases. Levels of an RXR-interacting protein in a sample may be assayed by any standard technique. For example, its expression may be monitored by standard Northern blot analysis or may be aided by PCR (see, e.g., Ausubel et al., supra; *PCR Technology: Principles and Applications for DNA Amplification*, ed., H. A. Ehrlich, Stcokton Press, NY). These techniques are enabled by the provision of the RXR-interacting protein sequences described herein. Alternatively, standard immunological or immunohistochemical procedures (e.g., those described above) may also be used with the antibodies described herein for RXR-interacting protein detection.

OTHER EMBODIMENTS

In other embodiments, the invention includes any protein which is substantially identical to a human RXR-interacting protein (FIGS. 4, 5, 10, and 11; SEQ ID NOS: 1–5); such homologs include other substantially pure naturally occurring mammalian RXR-interacting proteins (for example, human RXR-interacting proteins) as well as allelic variants; natural mutants; induced mutants; proteins encoded by DNA that hybridizes to the RXR-interacting protein DNA sequence of any of FIGS. 4, 5, 10, and 11 (SEQ ID NOS: 6–9, 14) under high stringency conditions or low stringency conditions (e.g., washing at 2×SSC at 40° C. with a probe length of at least 40 nucleotides); and polypeptides or proteins specifically bound by antisera directed to an RXR-interacting protein, especially by antisera to the RXR binding domain of the RXR-interacting protein. The term also includes chimeric polypeptides that include an RXR-interacting protein fragment.

The invention further includes analogs of any naturally occurring RXR-interacting protein. Analogs can differ from the naturally occurring RXR-interacting protein by amino acid sequence differences, by post-translational modifications, or by both. Analogs of the invention will generally exhibit at least 85%, more preferably 90%, and most preferably 95% or even 99% identity with all or part of a naturally occurring RXR-interacting protein sequence. The length of comparison sequences will be at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally occurring RXR-interacting protein by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, or Ausubel et al., supra). Also included are cyclized peptides molecules and analogs which contain residues other than L-amino acids, e.g., D-amino acids or non-naturally occurring or synthetic amino acids, e.g., β or γ amino acids.

In addition to full-length polypeptides, the invention also includes RXR-interacting protein fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of RXR-interacting proteins can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which facilitate interaction of the peptide with a retinoid X receptor.

All publications and patent applications mentioned in this specification are herein incorporated by reference to the same extent as if each independent publication or patent application was specifically and individually indicated to be incorporated by reference.

Other embodiments are within the following claims.

What is claimed is:

1. A substantially pure RXR-interacting protein, comprising an amino acid sequence that is at least 85% identical to the amino acid sequence of RIP15 (SEQ ID NO: 3).

2. The protein of claim 1, comprising an amino acid sequence that is at least 90% identical to the amino acid sequence of RIP15 shown in FIG. 5 (SEQ ID NO: 3).

3. The protein of claim 1, wherein said protein is derived from a mammal.

4. The protein of claim 3, wherein said mammal is a human.

5. The protein of claim 3, wherein said protein binds a β-retinoic acid response element (β-RARE) in the presence of RXR.

6. The protein of claim 3, wherein said protein binds an ecdysone response element (EcRE) in the presence of RXR.

7. RXR-interacting protein produced by expression of a purified DNA encoding a protein comprising an amino acid sequence that is at least 85% identical to the amino acid sequence of RIP15 (SEQ ID NO: 3).

8. The protein of claim 1, comprising an amino acid sequence that is at least 95% identical to the amino acid sequence of RIP15 (SEQ ID NO: 3).

9. The protein of claim 1, comprising an amino acid sequence that is identical to the amino acid sequence of RIP15 (SEQ ID NO: 3).

10. The protein of claim 1, wherein the amino acid sequence of said protein is identical to the amino acid sequence of RIP15 (SEQ ID NO: 3).

11. The protein of claim 1, said protein interacting with a retinoid X receptor in an in vivo interaction trap assay.

12. The protein of claim 1, said protein inhibiting retinoid X receptor-dependent activation of a β-RARE-linked nucleic acid.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 484 amino acids
      (B) TYPE: amino acid
      (C) STRANDEDNESS: Not Relevant
      (D) TOPOLOGY: linear (ii) MOLECULE TYPE: protein (xi) SEQUENCE DESCRIPTION: SEQ ID NO:1:

```
Met Val Met Gln Phe Gln Gly Leu Glu Asn Pro Ile Gln Ile Ser Leu
1               5                  10                  15

His His Ser His Arg Leu Ser Gly Phe Val Pro Asp Gly Met Ser Val
            20                  25                  30

Lys Pro Ala Lys Gly Met Leu Thr Glu His Ala Ala Gly Pro Leu Gly
        35                  40                  45

Gln Asn Leu Asp Leu Glu Ser Tyr Ser Pro Tyr Asn Asn Val Pro Phe
    50                  55                  60

Pro Gln Val Gln Pro Gln Ile Ser Ser Ser Ser Tyr Tyr Ser Asn Leu
```

-continued

```
              65                  70                  75                  80
Gly Phe Tyr Pro Gln Gln Pro Glu Asp Trp Tyr Ser Pro Gly Ile Tyr
                 85                  90                  95

Glu Leu Arg Arg Met Pro Ala Glu Thr Gly Tyr Gln Gly Glu Thr Glu
            100                 105                 110

Val Ser Glu Met Pro Val Thr Lys Lys Pro Arg Met Ala Ala Ala Ser
            115                 120                 125

Ala Gly Arg Ile Lys Gly Asp Glu Leu Cys Val Val Cys Gly Asp Arg
            130                 135                 140

Ala Ser Gly Tyr His Tyr Asn Ala Leu Thr Cys Glu Gly Cys Lys Gly
145                 150                 155                 160

Phe Phe Arg Arg Ser Ile Thr Lys Asn Ala Val Tyr Lys Cys Lys Asn
                165                 170                 175

Gly Gly Asn Cys Val Met Asp Met Tyr Met Arg Arg Lys Cys Gln Glu
                180                 185                 190

Cys Arg Leu Arg Lys Cys Arg Glu Met Gly Met Leu Ala Glu Cys Leu
            195                 200                 205

Leu Thr Glu Ile Gln Cys Lys Ser Lys Arg Leu Arg Lys Asn Val Lys
            210                 215                 220

Gln His Ala Asp Gln Thr Val Asn Glu Asp Asp Ser Glu Gly Arg Asp
225                 230                 235                 240

Leu Arg Gln Val Thr Ser Thr Lys Phe Cys Arg Glu Lys Thr Glu
                245                 250                 255

Leu Thr Ala Asp Gln Gln Thr Leu Leu Asp Tyr Ile Met Asp Ser Tyr
            260                 265                 270

Asn Lys Gln Arg Met Pro Gln Glu Ile Thr Asn Lys Ile Leu Lys Glu
            275                 280                 285

Glu Phe Ser Ala Glu Glu Asn Phe Leu Ile Leu Thr Glu Met Ala Thr
            290                 295                 300

Ser His Val Gln Ile Leu Val Glu Phe Thr Lys Lys Leu Pro Gly Phe
305                 310                 315                 320

Gln Thr Leu Asp His Glu Asp Gln Ile Ala Leu Leu Lys Gly Ser Ala
                325                 330                 335

Val Glu Ala Met Phe Leu Arg Ser Ala Glu Ile Phe Asn Lys Lys Leu
            340                 345                 350

Pro Ala Gly His Ala Asp Leu Leu Glu Glu Arg Ile Arg Lys Ser Gly
            355                 360                 365

Ile Ser Asp Glu Tyr Ile Thr Pro Met Phe Ser Phe Tyr Lys Ser Val
            370                 375                 380

Gly Glu Leu Lys Met Thr Gln Glu Glu Tyr Ala Leu Leu Thr Ala Ile
385                 390                 395                 400

Val Ile Leu Ser Pro Asp Arg Gln Tyr Ile Lys Asp Arg Glu Ala Val
                405                 410                 415

Glu Lys Leu Gln Glu Pro Leu Leu Asp Val Leu Gln Lys Leu Cys Lys
            420                 425                 430

Met Tyr Gln Pro Glu Asn Pro Gln His Phe Ala Cys Leu Leu Gly Arg
            435                 440                 445

Leu Thr Glu Leu Arg Thr Phe Asn His His Ala Glu Met Leu Met
            450                 455                 460

Ser Trp Arg Val Asn Asp His Lys Phe Thr Pro Leu Leu Cys Glu Ile
465                 470                 475                 480

Trp Asp Val Gln
```

-continued (2) INFORMATION FOR SEQ ID NO:2:

(i) SEQUENCE CHARACTERISTICS:
        (A) LENGTH: 451 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:2:

```
Met Leu Thr Glu His Ala Ala Gly Pro Leu Gly Gln Asn Leu Asp Leu
 1               5                  10                  15

Glu Ser Tyr Ser Pro Tyr Asn Asn Val Pro Phe Pro Gln Val Gln Pro
            20                  25                  30

Gln Ile Ser Ser Ser Tyr Tyr Ser Asn Leu Gly Phe Tyr Pro Gln
            35                  40                  45

Gln Pro Glu Asp Trp Tyr Ser Pro Gly Ile Tyr Glu Leu Arg Arg Met
        50                  55                  60

Pro Ala Glu Thr Gly Tyr Gln Gly Glu Thr Glu Val Ser Glu Met Pro
65                  70                  75                  80

Val Thr Lys Lys Pro Arg Met Ala Ala Ser Ala Gly Arg Ile Lys
                85                  90                  95

Gly Asp Glu Leu Cys Val Val Cys Gly Asp Arg Ala Ser Gly Tyr His
                100                 105                 110

Tyr Asn Ala Leu Thr Cys Glu Gly Cys Lys Gly Phe Phe Arg Arg Ser
            115                 120                 125

Ile Thr Lys Asn Ala Val Tyr Lys Cys Lys Asn Gly Gly Asn Cys Val
        130                 135                 140

Met Asp Met Tyr Met Arg Arg Lys Cys Gln Glu Cys Arg Leu Arg Lys
145                 150                 155                 160

Cys Arg Glu Met Gly Met Leu Ala Glu Cys Met Tyr Thr Gly Leu Leu
                165                 170                 175

Thr Glu Ile Gln Cys Lys Ser Lys Arg Leu Arg Lys Asn Val Lys Gln
            180                 185                 190

His Ala Asp Gln Thr Val Asn Glu Asp Asp Ser Glu Gly Arg Asp Leu
        195                 200                 205

Arg Gln Val Thr Ser Thr Thr Lys Phe Cys Arg Glu Lys Thr Glu Leu
    210                 215                 220

Thr Ala Asp Gln Gln Thr Leu Leu Asp Tyr Ile Met Asp Ser Tyr Asn
225                 230                 235                 240

Lys Gln Arg Met Pro Gln Glu Ile Thr Asn Lys Ile Leu Lys Glu Glu
                245                 250                 255

Phe Ser Ala Glu Glu Asn Phe Leu Ile Leu Thr Glu Met Ala Thr Ser
            260                 265                 270

His Val Gln Ile Leu Val Glu Phe Thr Lys Lys Leu Pro Gly Phe Gln
        275                 280                 285

Thr Leu Asp His Glu Asp Gln Ile Ala Leu Leu Lys Gly Ser Ala Val
    290                 295                 300

Glu Ala Met Phe Leu Arg Ser Ala Glu Ile Phe Asn Lys Lys Leu Pro
305                 310                 315                 320

Ala Gly His Ala Asp Leu Leu Glu Glu Arg Ile Arg Lys Ser Gly Ile
                325                 330                 335

Ser Asp Glu Tyr Ile Thr Pro Met Phe Ser Phe Tyr Lys Ser Val Gly
            340                 345                 350
```

```
Glu Leu Lys Met Thr Gln Glu Tyr Ala Leu Leu Thr Ala Ile Val
            355                 360                 365

Ile Leu Ser Pro Asp Arg Gln Tyr Ile Lys Asp Arg Glu Ala Val Glu
370                 375                 380

Lys Leu Gln Glu Pro Leu Leu Asp Val Leu Gln Lys Leu Cys Lys Met
385                 390                 395                 400

Tyr Gln Pro Glu Asn Pro Gln His Phe Ala Cys Leu Leu Gly Arg Leu
                405                 410                 415

Thr Glu Leu Arg Thr Phe Asn His His His Ala Glu Met Leu Met Ser
            420                 425                 430

Trp Arg Val Asn Asp His Lys Phe Thr Pro Leu Leu Cys Glu Ile Trp
            435                 440                 445

Asp Val Gln
    450
```

(2) INFORMATION FOR SEQ ID NO:3:

(i) SEQUENCE CHARACTERISTICS:
        (A) LENGTH: 446 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:3:

```
Met Ser Ser Pro Thr Ser Ser Leu Asp Thr Pro Val Pro Gly Asn Gly
1               5                   10                  15

Ser Pro Gln Pro Ser Thr Ser Ala Thr Ser Pro Thr Ile Lys Glu Glu
            20                  25                  30

Gly Gln Glu Thr Asp Pro Pro Gly Ser Glu Gly Ser Ser Ser Ala
            35                  40                  45

Tyr Ile Val Val Ile Leu Glu Pro Glu Asp Glu Pro Glu Arg Lys Arg
    50                  55                  60

Lys Lys Gly Pro Ala Pro Lys Met Leu Gly His Glu Leu Cys Arg Val
65                  70                  75                  80

Cys Gly Asp Lys Ala Ser Gly Phe His Tyr Asn Val Leu Ser Cys Glu
                85                  90                  95

Gly Cys Lys Gly Phe Phe Arg Arg Ser Val Val His Gly Gly Ala Gly
            100                 105                 110

Arg Tyr Ala Cys Arg Gly Ser Gly Thr Cys Gln Met Asp Ala Phe Met
            115                 120                 125

Arg Arg Lys Cys Gln Leu Cys Arg Leu Arg Lys Cys Lys Glu Ala Gly
            130                 135                 140

Met Arg Glu Gln Cys Val Leu Ser Glu Glu Gln Ile Arg Lys Lys Arg
145                 150                 155                 160

Ile Gln Lys Gln Gln Gln Gln Pro Pro Pro Ser Glu Pro Ala
                165                 170                 175

Ala Ser Ser Ser Gly Arg Pro Ala Ala Ser Pro Gly Thr Ser Glu Ala
            180                 185                 190

Ser Ser Gln Gly Ser Gly Glu Gly Glu Gly Ile Gln Leu Thr Ala Ala
            195                 200                 205

Gln Glu Leu Met Ile Gln Gln Leu Val Ala Ala Gln Leu Gln Cys Asn
            210                 215                 220

Lys Arg Ser Phe Ser Asp Gln Pro Lys Val Thr Pro Trp Pro Leu Gly
225                 230                 235                 240
```

```
Ala Asp Pro Gln Ser Arg Asp Ala Arg Gln Gln Arg Phe Ala His Phe
            245                 250                 255

Thr Glu Leu Ala Ile Ile Ser Val Gln Glu Ile Val Asp Phe Ala Lys
                260                 265                 270

Gln Val Pro Gly Phe Leu Gln Leu Gly Arg Glu Asp Gln Ile Ala Leu
            275                 280                 285

Leu Lys Ala Ser Thr Ile Glu Ile Met Leu Leu Gln Thr Ala Arg Arg
290                 295                 300

Tyr Asn His Glu Thr Glu Cys Ile Thr Phe Leu Lys Asp Phe Thr Tyr
305                 310                 315                 320

Ser Lys Asp Asp Phe His Arg Ala Gly Leu Gln Val Glu Phe Ile Asn
                325                 330                 335

Pro Ile Phe Glu Phe Ser Arg Ala Met Arg Arg Leu Gly Leu Asp Asp
            340                 345                 350

Ala Glu Tyr Ala Leu Leu Ile Ala Ile Asn Ile Phe Ser Ala Asp Arg
            355                 360                 365

Pro Asn Val Gln Glu Pro Ser Arg Val Glu Ala Leu Gln Gln Pro Tyr
370                 375                 380

Val Glu Ala Leu Leu Ser Tyr Thr Arg Ile Lys Arg Pro Gln Asp Gln
385                 390                 395                 400

Leu Arg Phe Pro Arg Met Leu Met Lys Leu Val Ser Leu Arg Thr Leu
                405                 410                 415

Ser Ser Val His Ser Glu Gln Val Phe Ala Leu Arg Leu Gln Asp Lys
                420                 425                 430

Lys Leu Pro Pro Leu Leu Ser Glu Ile Trp Asp Val His Glu
            435                 440                 445

(2) INFORMATION FOR SEQ ID NO:4:

(i) SEQUENCE CHARACTERISTICS:
        (A) LENGTH: 716 amino acids
        (B) TYPE: amino acid
        (C) STRANDEDNESS: single
        (D) TOPOLOGY: linear (ii) MOLECULE TYPE: DNA (xi) SEQUENCE DESCRIPTION: SEQ ID NO:4:

Ser Pro Ser Cys Gly Phe Gln Arg Lys Asp Leu Glu Thr Ser Ser Cys
1               5                   10                  15

Val Ser Ile Lys Lys Lys Arg Arg Leu Glu Asp Leu Leu Ile Val Ile
                20                  25                  30

Ser Asp Ser Asp Gly Glu Glu Thr Lys Glu Glu Asn Gly Leu Gln Lys
            35                  40                  45

Thr Lys Thr Lys Gln Ser Asn Arg Ser Lys Cys Leu Ala Lys Arg Lys
50                  55                  60

Val Ala His Met Ser Glu Glu Gln Phe Ala Leu Ala Leu Lys Met
65                  70                  75                  80

Ser Glu Gln Glu Ala Arg Glu Val Asn Asn Gln Glu Glu Lys Glu Glu
                85                  90                  95

Glu Leu Leu Arg Lys Ala Ile Ala Glu Ser Leu Asn Ser Cys Trp Ser
            100                 105                 110

Ser Ala Ala Ser Ala Thr Arg Ser Arg Pro Leu Ala Ala Glu Leu Ser
            115                 120                 125

Ser His Ser His Gln Glu Asn Thr Lys Asp Ser Gly Thr Thr Glu Gly
            130                 135                 140
```

-continued

| | | | | | | | | | | | | | | | |
|---|---|---|---|---|---|---|---|---|---|---|---|---|---|---|---|
|Val|Trp|Gln|Leu|Val|Pro|Pro|Ser|Leu|Cys|Lys|Gly|Ser|His|Val|Ser|
|145| | | | |150| | | |155| | | |160| | |
|Gln|Gly|Asn|Glu|Ala|Glu|Gln|Arg|Lys|Glu|Pro|Trp|Asp|His|Asn|Glu|
| | | | |165| | | |170| | | |175| | | |
|Asn|Thr|Glu|Glu|Glu|Pro|Val|Ser|Gly|Ser|Ser|Gly|Ser|Trp|Asp|Gln|
| | | |180| | | | |185| | | |190| | | |
|Ser|Ser|Gln|Pro|Val|Phe|Glu|Asn|Glu|Asn|Val|Lys|Cys|Phe|Asp|Arg|
| | |195| | | | |200| | | | |205| | | |
|Cys|Thr|Gly|His|Leu|Ala|Glu|His|Thr|Gln|Cys|Gly|Lys|Pro|Gln|Glu|
|210| | | | |215| | | |220| | | | | | |
|Ser|Thr|Gly|Ser|Gly|Tyr|Ala|Phe|Ser|Lys|Ala|Val|Gln|Gly|Arg|Gly|
|225| | | | |230| | | |235| | | | |240| |
|Asp|Thr|Ser|Arg|Gln|Cys|Leu|Pro|Ile|Pro|Ala|Asp|Thr|Lys|Gly|Leu|
| | | |245| | | | |250| | | | |255| | |
|Gln|Asp|Thr|Gly|Gly|Thr|Val|His|Tyr|Tyr|Trp|Gly|Ile|Pro|Phe|Cys|
| | | |260| | | | |265| | | |270| | | |
|Pro|Ala|Gly|Val|Asp|Pro|Asn|Gln|Tyr|Thr|Asn|Val|Ile|Leu|Cys|Gln|
| | |275| | | | |280| | | | |285| | | |
|Leu|Glu|Val|Tyr|Gln|Lys|Ser|Leu|Lys|Met|Ala|Gln|Arg|Gln|Leu|Val|
| |290| | | | |295| | | |300| | | | | |
|Lys|Lys|Arg|Gly|Phe|Gly|Glu|Pro|Val|Leu|Pro|Arg|Pro|Pro|Phe|Leu|
|305| | | |310| | | |315| | | | |320| | |
|Ile|Gln|Asn|Glu|Cys|Gly|Gln|Glu|Asp|Gln|Thr|Ser|Asp|Lys|Asn|Glu|
| | | | |325| | | |330| | | |335| | | |
|Gly|Ile|Ser|Glu|Asp|Met|Gly|Asp|Glu|Ala|Lys|Glu|Arg|Gln|Glu|
| | | |340| | | |345| | | |350| | | | |
|Ser|Arg|Ala|Ser|Val|Trp|His|Ser|Glu|Thr|Lys|Asp|Phe|Gln|Lys|Ser|
| |355| | | | |360| | | |365| | | | | |
|Pro|Ile|Lys|Ser|Leu|Lys|Gln|Lys|Leu|Leu|Glu|Glu|Pro|Thr|
|370| | | | |375| | | |380| | | | | | |
|Thr|Ser|Arg|Gly|Gln|Ser|Ser|Gln|Gly|Leu|Phe|Val|Glu|Glu|Thr|Ser|
|385| | | |390| | | | |395| | | | |400| |
|Glu|Glu|Gly|Leu|Lys|Ser|Ser|Glu|Gly|Asp|Asn|Ser|Val|Pro|Thr|Thr|
| | | |405| | | | |410| | | | |415| | |
|Gln|Ser|Ile|Ala|Ala|Leu|Thr|Ser|Lys|Arg|Ser|Leu|Val|Leu|Met|Pro|
| | |420| | | | |425| | | | |430| | | |
|Glu|Ser|Ser|Ala|Glu|Glu|Ile|Thr|Val|Cys|Pro|Glu|Thr|Gln|Leu|Ser|
| |435| | | | |440| | | |445| | | | | |
|Phe|Leu|Glu|Pro|Leu|Asp|Leu|Asn|Arg|Glu|Asp|Ser|Pro|Asp|Ser|Arg|
|450| | | | |455| | | |460| | | | | | |
|Glu|Leu|Pro|Ile|Glu|Val|Arg|Met|Ala|Val|Gly|Asp|Lys|Gln|Val|Ala|
|465| | | |470| | | |475| | | | |480| | |
|Asn|Arg|Glu|Asp|Cys|Met|Lys|Glu|Asn|Pro|Pro|Ala|Val|Ser|Ser|
| | | |485| | | | |490| | | | |495| | |
|Ser|Thr|Arg|Val|Ser|Cys|Pro|Leu|Cys|Asn|Gln|Asp|Phe|Pro|Pro|Thr|
| | |500| | | | |505| | | | |510| | | |
|Lys|Ile|Glu|Gln|His|Ala|Met|Tyr|Cys|Asn|Gly|Leu|Met|Glu|Gln|Glu|
| |515| | | | |520| | | |525| | | | | |
|Thr|Val|Leu|Thr|Arg|Arg|Arg|Glu|Ala|Lys|Asn|Lys|Ser|Asp|Gly|
| |530| | | | |535| | | |540| | | | | |
|Arg|Thr|Ala|Ala|Gln|Pro|Ala|Leu|Asp|Ala|Asn|Arg|Lys|Glu|Lys|Cys|
|545| | | |550| | | |555| | | | |560| | |
|Tyr|Leu|Cys|Lys|Ser|Leu|Val|Pro|Leu|Gly|Glu|Tyr|Gln|Cys|His|Val|

```
                    565                 570                 575
Glu Ala Cys Leu Gln Leu Ala Lys Val Asp Arg Glu Asp Gly Ile Glu
                580                 585                 590
Gly Thr Arg Arg Pro Arg Val Cys Ala Pro Val Glu Gly Lys Gln Gln
            595                 600                 605
Gln Arg Leu Lys Lys Ser Lys Asp Lys Gly His Ser Gln Gly Arg Leu
        610                 615                 620
Leu Ser Leu Leu Glu Gln Ser Glu His Arg Thr Thr Gly Val Glu Lys
625                 630                 635                 640
Lys Pro Lys Tyr Ser Glu Val Arg Thr Phe Arg Met Pro Ser Pro Glu
                645                 650                 655
Val Glu Glu Ala Ser Cys Ser Arg Glu Met Gln Ser Thr Leu Ser Gln
                660                 665                 670
Leu Asn Leu Asn Glu Ser Pro Ile Lys Ser Phe Val Pro Val Ser Glu
            675                 680                 685
Ala Thr Asn Cys Leu Val Asp Phe Lys Glu Gln Phe Ala Phe Arg Ser
        690                 695                 700
Arg Thr Lys Ser Gly Arg Glu Arg Arg Lys Ser
705                 710                 715

(2) INFORMATION FOR SEQ ID NO:5:

(i) SEQUENCE CHARACTERISTICS:
        (A) LENGTH: 619 amino acids
        (B) TYPE: amino acid
        (C) STRANDEDNESS: single
        (D) TOPOLOGY: linear (ii) MOLECULE TYPE: DNA (xi) SEQUENCE DESCRIPTION: SEQ ID NO:5:

Asp Ala Leu Ala Ala Leu Val Asp Ala Ala Ala Ser Ala Pro Gln Met
1               5                   10                  15

Asp Val Ser Lys Thr Lys Glu Ser Lys His Glu Ala Ala Arg Leu Glu
                20                  25                  30

Glu Asn Leu Arg Ser Arg Ser Ala Ala Val Ser Glu Gln Gln Gln Leu
            35                  40                  45

Glu Gln Lys Asn Leu Glu Val Glu Lys Arg Ser Val Gln Cys Val Cys
        50                  55                  60

Thr Ser Ser Ala Leu Pro Ser Gly Lys Ala Gln Pro His Ala Ser Val
65                  70                  75                  80

Val Tyr Ser Glu Ala Gly Lys Asp Lys Gly Pro Pro Lys Ser Arg
                85                  90                  95

Tyr Glu Glu Glu Leu Arg Thr Arg Gly Lys Thr Thr Ile Thr Ala Ala
                100                 105                 110

Asn Phe Ile Asp Val Thr Ile Thr Arg Gln Ile Ala Ser Asp Lys Asp
            115                 120                 125

Ala Arg Glu Arg Gly Ser Gln Ser Ser Asp Ser Ser Ser Leu Ser
        130                 135                 140

Ser His Arg Tyr Glu Thr Ala Ser Asp Ala Ile Glu Val Ile Ser Pro
145                 150                 155                 160

Ala Ser Ser Pro Ala Pro Pro Gln Glu Lys Pro Gln Ala Tyr Gln Pro
                165                 170                 175

Asp Met Val Lys Ala Asn Gln Ala Glu Asn Glu Ser Thr Arg Gln Tyr
            180                 185                 190

Glu Gly Pro Leu His His Tyr Arg Ser Gln Gln Glu Ser Pro Ser Pro
```

-continued

```
            195                 200                 205
Gln Gln Gln Pro Pro Leu Pro Ser Ser Gln Ser Glu Gly Met Gly
    210                 215                 220

Gln Val Pro Arg Thr His Arg Leu Ile Thr Leu Ala Asp His Ile Cys
225                 230                 235                 240

Gln Ile Ile Thr Gln Asp Phe Ala Arg Asn Gln Val Pro Ser Gln Pro
                245                 250                 255

Ser Thr Ser Thr Phe Gln Thr Ser Pro Ser Ala Leu Ser Ser Thr Pro
                260                 265                 270

Val Arg Thr Lys Thr Ser Ser Arg Tyr Ser Pro Glu Ser Gln Ser Gln
            275                 280                 285

Thr Val Leu His Pro Arg Pro Gly Pro Arg Val Ser Pro Glu Asn Leu
            290                 295                 300

Val Asp Lys Ser Arg Gly Ser Arg Pro Gly Lys Ser Pro Glu Arg Ser
305                 310                 315                 320

His Ile Pro Ser Glu Pro Tyr Glu Pro Ile Ser Pro Pro Gln Gly Pro
                325                 330                 335

Ala Val His Glu Lys Gln Asp Ser Met Leu Leu Ser Gln Arg Gly
                340                 345                 350

Val Asp Pro Ala Glu Gln Arg Ser Asp Ser Arg Ser Pro Gly Ser Ile
            355                 360                 365

Ser Tyr Leu Pro Ser Phe Phe Thr Lys Leu Glu Ser Thr Ser Pro Met
            370                 375                 380

Val Lys Ser Lys Lys Gln Glu Ile Phe Arg Lys Leu Asn Ser Ser Gly
385                 390                 395                 400

Gly Gly Asp Ser Asp Met Ala Ala Ala Gln Pro Gly Thr Glu Ile Phe
                405                 410                 415

Asn Leu Pro Ala Val Thr Thr Ser Gly Ala Val Ser Ser Arg Ser His
                420                 425                 430

Ser Phe Ala Asp Pro Ala Ser Asn Leu Gly Leu Glu Asp Ile Ile Arg
            435                 440                 445

Lys Ala Leu Met Gly Ser Phe Asp Asp Lys Val Glu Asp His Gly Val
    450                 455                 460

Val Met Ser His Pro Val Gly Ile Met Pro Gly Ser Ala Ser Thr Ser
465                 470                 475                 480

Val Val Thr Ser Ser Glu Ala Arg Arg Asp Glu Gly Glu Pro Ser Pro
                485                 490                 495

His Ala Gly Val Cys Lys Pro Lys Leu Ile Asn Lys Ser Asn Ser Arg
                500                 505                 510

Lys Ser Lys Ser Pro Ile Pro Gly Gln Ser Tyr Leu Gly Thr Glu Arg
            515                 520                 525

Pro Ser Ser Val Ser Ser Val His Ser Glu Gly Asp Tyr His Arg Gln
    530                 535                 540

Thr Pro Gly Trp Ala Trp Glu Asp Arg Pro Ser Ser Thr Gly Ser Thr
545                 550                 555                 560

Gln Phe Pro Tyr Asn Pro Leu Thr Ile Arg Met Leu Ser Ser Thr Pro
                565                 570                 575

Pro Thr Gln Ile Ala Cys Ala Pro Ser Ala Ile Thr Gln Ala Ala Pro
                580                 585                 590

His Gln Gln Asn Arg Ile Trp Glu Arg Glu Pro Ala Pro Leu Leu Ser
            595                 600                 605

Ala Gln Tyr Glu Thr Leu Ser Asp Ser Asp Asp
    610                 615
```

(2) INFORMATION FOR SEQ ID NO:6:

(i) SEQUENCE CHARACTERISTICS:
        (A) LENGTH: 1787 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

```
GGAAGCTAAG GATGGTGATG CAGTTTCAGG GCTTAGAAAA TCCAATTCAG ATTAGTCTTC    60
ACCACAGCCA CCGGCTGTCA GGATTTGTGC CGGACGGGAT GAGTGTGAAG CCAGCTAAAG   120
GTATGCTAAC AGAACACGCG GCAGGCCCTC TGGGGCAGAA TCTGGATTTG GAATCGTACT   180
CCCCATACAA CAATGTCCCG TTTCCTCAAG TTCAGCCACA GATTTCCTCC TCGTCTTACT   240
ATTCCAACCT GGGCTTCTAC CCCCAACAAC CGGAAGACTG GTATTCTCCT GGCATCTATG   300
AACTCAGGCG AATGCCCGCT GAGACTGGGT ACCAGGGAGA GACTGAGGTA TCAGAGATGC   360
CTGTGACAAA GAAGCCGCGA ATGGCCGCGG CATCGGCAGG CAGAATAAAA GGGGATGAGC   420
TGTGTGTTGT CTGTGGAGAC AGGGCCTCTG GGTACCACTA CAACGCGCTC ACCTGTGAGG   480
GCTGCAAAGG TTTCTTCCGA AGAAGCATTA CCAAGAACGC CGTGTACAAG TGTAAGAACG   540
GGGCAACTG  CGTGATGGAC ATGTACATGC GCAGGAAGTG CCAGGAGTGC CGGCTAAGGA   600
AGTGCAGAGA GATGGGGATG TTGGCTGAAT GTTTGTTAAC TGAAATCCAG TGTAAATCTA   660
AACGGCTAAG GAAAAATGTG AAGCAGCACG CTGATCAGAC AGTGAATGAG GACGACAGCG   720
AAGGGCGTGA CTTGCGACAA GTGACCTCCA CAACCAAGTT TTGCAGGGAG AAAACGGAAC   780
TCACGGCAGA CCAGCAGACC CTCCTGGATT ATATTATGGA TTCGTACAAC AAACAGAGAA   840
TGCCTCAGGA AATCACAAAT AAAATCTTAA AGAAGAATT  TAGTGCAGAA GAAAATTTTC   900
TCATATTAAC AGAAATGGCA ACCAGCCATG TACAGATTCT CGTAGAATTC ACAAAAAAGC   960
TTCCAGGGTT TCAGACACTG GACCACGAAG ATCAGATTGC TTTGCTCAAA GGGTCCGCAG  1020
TGGAGGCCAT GTTTCTTCGT TCGGCGGAGA TTTTCAATAA GAAACTTCCT GCCGGACATG  1080
CAGACCTGTT GGAAGAAAGA ATTCGAAAGA GTGGTATCTC TGATGAGTAT ATAACCCCGA  1140
TGTTCAGTTT CTATAAAAGT GTTGGAGAAC TCAAAATGAC TCAGGAGGAG TACGCTCTGC  1200
TCACAGCGAT CGTCATCCTC TCTCCAGACA GACAATACAT CAAGGACAGA GAGGCGGTGG  1260
AGAAGCTGCA GGAGCCCCTG CTTGATGTGC TACAAAAGCT GTGCAAGATG TACCAGCCTG  1320
AGAACCCACA GCATTTCGCC TGCCTCCTGG GTCGCCTGAC GGAACTCCGG ACATTCAACC  1380
ATCACCACGC TGAGATGCTG ATGTCTTGGA GAGTGAATGA TCACAAGTTC ACCCCGCTCC  1440
TCTGTGAGAT CTGGGATGTG CAGTGATGGA CACCAGTGGG GCTGGCTCCT TGTCCTCCTC  1500
GGAACAGAAA CCTTGTTTCG TTTGTACCTG GTTTCACTCA AGAATCTCAA TGAATATTTA  1560
TGTGGCAATT ATACACCTCC CACGGTTGTA AATACAGACT AGATAGAACT GCTTTCCCCA  1620
CACTGTATTT TACAAGGCTT CAGGAAACCC CACTGGCATG CCCTTTTGGC CTAATTAAAT  1680
CAATTGTTAC TTCAATTCTA TCTACTGAGC TAGGGGCATA TTATTCTTCA TTCGACAATA  1740
TTATATATAT TTTATAAAGT TGAGCTGTTT TCAACTGAGA CAATAAA              1787
```

(2) INFORMATION FOR SEQ ID NO:7:

(i) SEQUENCE CHARACTERISTICS:
        (A) LENGTH: 1860 base pairs (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
GCCAGGGCAA CAGAGTCGGA GACCCCCTGC CACCCCCTC  CCGATCGCCG GTGCAGTCAT    60
GAGCCCCGCC TCCCCCTGGT GCACGGAGAG GGGCGGGGCC TGGAACAAGC AGGCTGCTTC   120
GTGACCCACT ATGTCTTCCC CCACAAGTTC TCTGGACACT CCCGTGCCTG GAATGGTTC    180
TCCTCAGCCC AGTACCTCCG CCACGTCACC CACTATTAAG GAAGAGGGGC AGGAGACTGA   240
TCCTCCTCCA GGCTCTGAAG GGTCCAGCTC TGCCTACATC GTGGTCATCT TAGAGCCAGA   300
GGATGAGCCT GAGCGCAAGC GGAAGAAGGG GCCGGCCCCG AAGATGCTGG GCCATGAGCT   360
GTGCCGCGTG TGCGGAGACA AGGCTTCGGG CTTCCACTAC AACGTGCTCA GCTGTGAAGG   420
CTGCAAAGGC TTCTTCCGGC GCAGTGTGGT CCACGGTGGG GCCGGGCGCT ATGCCTGTCG   480
GGGCAGCGGA ACCTGCCAGA TGGATGCCTT CATGCGGCGC AAGTGCCAGC TCTGCCGGCT   540
GCGCAAGTGC AAGGAGGCTG GCATGCGGGA GCAGTGCGTG CTCTCTGAGG AGCAGATTCG   600
GAAGAAAAGG ATTCAGAAGC AGCAACAGCA GCAGCCACCA CCCCCATCTG AGCCAGCAGC   660
CAGCAGCTCA GGCCGGCCAG CGGCCTCCCC TGGCACTTCG GAAGCAAGCA GCCAGGGCTC   720
CGGGGAAGGA GAGGGCATCC AGCTGACCGC GGCTCAGGAG CTGATGATCC AGCAGTTAGT   780
TGCCGCGCAG CTGCAGTGCA ACAAACGATC TTTCTCCGAC CAGCCCAAAG TCACGCCCTG   840
GCCCCTGGGT GCAGACCCTC AGTCCCGAGA TGCCCGTCAG CAACGCTTTG CCCACTTCAC   900
CGAGCTAGCC ATCATCTCGG TCCAGGAGAT TGTGGACTTT GCCAAGCAGG TGCCAGGGTT   960
CTTGCAGTTG GGCCGGGAGG ACCAGATCGC CCTCCTGAAG GCGTCCACCA TTGAGATCAT  1020
GTTGCTACAA ACAGCCAGAC GCTACAACCA CGAGACAGAA TGCATCACGT TCCTGAAGGA  1080
CTTCACCTAC AGCAAGGACG ACTTCCACCG TGCAGGCTTG CAGGTGGAAT TCATCAATCC  1140
CATCTTCGAG TTCTCGCGGG CCATGCGGCG GCTGGGCCTG GACGATGCAG AGTATGCCTT  1200
GCTTATCGCC ATCAACATCT TCTCAGCCGA TCGGCCTAAT GTGCAGGAGC CAGCCGTGT   1260
GGAGGCCCTG CAGCAGCCCT ACGTGGAGGC GCTCCTCTCC TACACGAGGA TCAAGCGCCC  1320
ACAGGACCAG CTCCGCTTCC CACGCATGCT CATGAAGCTG GTGAGCCTGC GCACCCTCAG  1380
CTCCGTGCAC TCGGAGCAGG TCTTTGCATT GCGACTCCAG GACAAGAAGC TGCCGCCCTT  1440
GCTGTCCGAG ATCTGGGATG TGCACGAGTA GGGGCAGCCA CAAGTGCCCC AGCCTTGGTG  1500
GTGTCTTCTT GAAGATGGAC TCTTCACCTC TCCTCCTGGG GTGGGAGGAC ATTGTCACGG  1560
CCCAGTCCCT CGGGCTCAGC CTCAAACTCA GCGGCAGTTG GCACTAAGAA GGCCCCACCC  1620
CACCCATTGA GTCTTCCAAG AGTGGTGAGG GTCACAGGTC CTAGCCTCTG ACCGTTCCCA  1680
GCTGCCCTCC CACCCACGCT TACACCTCAG CCTACCACAC CATGCACCTT GAGTGGAGAG  1740
AGGTTAGGGC AGGTGGCCCC CCACAGTTGG GAGACCACAG GCCCTCTCTT CTGCCCCTTT  1800
TATTTAATAA AAAACAAAA  ATAAAGTTTG AGTACAAGCC AAAAAAAAAA AAAAAAAAA   1860
```

(2) INFORMATION FOR SEQ ID NO:8:

(i) SEQUENCE CHARACTERISTICS:
        (A) LENGTH: 2389 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

| | | | | | |
|---|---|---|---|---|---|
| TCTCCAAGTT | GTGGCTTTCA | GAGGAAGGAT | CTGGAAACAA | GCAGTTGTGT | CAGTATAAAG | 60 |
| AAGAAGCGTA | GACTTGAGGA | CTTACTCATA | GTGATATCCG | ATAGCGATGG | AGAGGAAACA | 120 |
| AAAGAGGAGA | ATGGATTGCA | GAAAACGAAG | ACAAAACAGT | CGAACAGATC | AAAGTGTTTG | 180 |
| GCTAAAAGAA | AAGTTGCACA | CATGTCAGAA | GAAGAACAAT | TTGCTTTGGC | TCTCAAGATG | 240 |
| AGTGAGCAGG | AAGCTAGGGA | GGTGAATAAC | CAGGAGGAGA | AAGAAGAGGA | GCTCTTGCGG | 300 |
| AAAGCCATTG | CTGAAAGCCT | GAATAGTTGC | TGGTCTTCTG | CTGCTTCTGC | TACCAGATCT | 360 |
| CGACCTCTGG | CTGCTGAACT | ATCTTCACAT | TCCCATCAAG | AGAACACCAA | AGACTCTGGG | 420 |
| ACCACTGAAG | GCGTATGGCA | GCTGGTACCT | CCATCACTGT | GTAAAGGCTC | ACATGTCAGT | 480 |
| CAGGGAAACG | AGGCTGAGCA | AAGAAAGGAG | CCCTGGGACC | ACAATGAAAA | CACTGAAGAG | 540 |
| GAGCCGGTCT | CTGGCAGCTC | AGGAAGCTGG | GACCAGTCAA | GCCAGCCAGT | GTTTGAGAAT | 600 |
| GAGAACGTTA | AATGTTTTGA | CAGATGTACT | GGCCACTTGG | CTGAGCACAC | ACAGTGTGGG | 660 |
| AAGCCACAGG | AAAGTACTGG | GAGTGGTTAT | GCTTTTTCCA | AAGCTGTCCA | GGGTAGGGGG | 720 |
| GACACGTCTA | GGCAATGCCT | TCCTATCCCA | GCAGACACAA | AAGGTCTCCA | GGACACTGGG | 780 |
| GGCACTGTGC | ACTACTACTG | GGGTATTCCA | TTCTGCCCTG | CTGGAGTAGA | TCCCAATCAA | 840 |
| TACACCAATG | TCATTCTCTG | CCAGTTAGAG | GTTTATCAGA | AGAGCCTGAA | AATGGCTCAG | 900 |
| AGACAGCTTG | TTAAAAAAAG | AGGGTTTGGG | GAACCAGTGT | TACCTAGACC | TCCTTTTCTG | 960 |
| ATCCAGAATG | AATGTGGCCA | AGAAGATCAG | ACTAGTGACA | AAAATGAAGG | CATCTCAGAA | 1020 |
| GATATGGGAG | ATGAAGCCAA | AGAGGAAAGG | CAGGAATCTA | GGGCATCTGT | CTGGCACTCA | 1080 |
| GAAACCAAGG | ATTTTCAAAA | AAGTCCAATT | AAAAGCTTGA | ACAGAAACT | TTTGTTGGAG | 1140 |
| GAAGAACCAA | CAACCAGTCG | TGGTCAGTCT | TCCCAAGGTC | TGTTTGTTGA | AGAAACCTCT | 1200 |
| GAAGAAGGTC | TGAAGAGTTC | GGAAGGAGAC | AACTCTGTGC | CCACCACGCA | AAGCATTGCA | 1260 |
| GCTTTGACCA | GTAAGAGAAG | TTTAGTTCTT | ATGCCGGAAA | GTTCTGCAGA | GAAAATCACT | 1320 |
| GTTTGCCCTG | AGACACAGTT | AAGTTTCCTT | GAACCCCTTG | ACCTCAATAG | AGAAGACTCT | 1380 |
| CCAGATAGCA | GAGAGCTCCC | CATTGAAGTA | AGGATGGCAG | TGGGCGATAA | GCAGGTTGCT | 1440 |
| AATAGGGAAG | ATTGTATGAA | GGAAAACCCT | CCTCCTGCAG | TCTCATCTAG | TACCCGGGTA | 1500 |
| TCCTGCCCAC | TGTGTAACCA | AGACTTTCCT | CCCACAAAGA | TTGAACAGCA | TGCCATGTAC | 1560 |
| TGCAATGGTC | TGATGGAGCA | GGAAACAGTG | TTGACTCGGA | GACGAAGAGA | GGCCAAGAAC | 1620 |
| AAGAGTGACG | GTCGGACAGC | TGCACAGCCG | GCTCTGGATG | CCAACAGGAA | GGAGAAGTGT | 1680 |
| TATCTATGTA | AGTCCCTGGT | TCCACTTGGG | GAGTATCAGT | GCCATGTGGA | GGCCTGTCTC | 1740 |
| CAGCTTGCAA | AGGTTGACAG | AGAAGATGGG | ATTGAAGGGA | CAAGGAGACC | AAGGGTGTGT | 1800 |
| GCACCTGTGG | AGGGGAAACA | ACAGCAGCGG | CTGAAGAAGT | CAAAGGACAA | AGGCCATAGT | 1860 |
| CAAGGCCGAC | TCCTCAGTCT | CTTGGAGCAG | TCTGAGCATA | GGACCACAGG | TGTAGAGAAA | 1920 |
| AAACCCAAGT | ATTCGGAAGT | AAGAACCTTC | AGGATGCCCT | CACCAGAGGT | GGAAGAGGCT | 1980 |
| AGCTGCAGCA | GAGAGATGCA | GAGTACCCTC | TCACAGCTCA | ACTTAAATGA | GTCTCCCATC | 2040 |
| AAGTCTTTTG | TTCCTGTTTC | AGAAGCTACA | AATTGCTTAG | TGGACTTTAA | AGAACAGTTT | 2100 |
| GCTTTCCGGT | CACGAACTAA | ATCAGGCAGG | GAAAGGAGGA | GAAAATCTTG | AATTTCTTGA | 2160 |
| GACTGGAAGG | TTGACCAGAA | CACACATCGT | TGGGTTGATC | GTGTTCATTA | AGTATAGTGG | 2220 |
| TCTCTAGTTT | GTGGTGAGAG | TTCTGACCCT | GTTGTTATCA | CCACCAGCAC | CCATTCAGTA | 2280 |

```
TCCTGGCTTT ATATTTTATA AGATCAGTTC AGACAACTGT GAATATTATT CTGTTTGAAT      2340

TTGCTTATAG TTAAAATTTA AATATATTTA TCTTTGTATG AAAAAAAAA                  2389

(2) INFORMATION FOR SEQ ID NO:9:

(i) SEQUENCE CHARACTERISTICS:
        (A) LENGTH: 1922 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

GGATGCCCTG GCTGCTCTTG TGGATGCTGC AGCTTCTGCA CCCCAGATGG ATGTTTCCAA        60

AACAAAAGAG AGTAAGCATG AAGCTGCCAG GTTAGAAGAA AATTTGAGAA GCAGGTCAGC       120

AGCAGTTAGT GAACAGCAGC AGCTAGAGCA GAAAAACCTG GAGGTGGAGA AGAGATCTGT       180

TCAGTGTGTG TGCACTTCTT CAGCCCTTCC AAGTGGCAAG GCCCAGCCTC ATGCCTCAGT       240

AGTGTATTCT GAGGCTGGGA AAGATAAAGG GCCTCCTCCA AAATCCAGAT ATGAGGAAGA       300

GCTAAGGACC CGAGGGAAGA CTACCATTAC TGCAGCTAAC TTCATAGACG TGACCATCAC       360

CCGGCAAATT GCCTCGGACA AGGATGCGAG GGAACGTGGC TCTCAAAGTT CAGACTCTTC       420

TAGTAGCTTG TCTTCTCACA GGTATGAAAC GGCTAGTGAT GCCATTGAGG TGATAAGTCC       480

CGCCAGCTCA CCTGCACCAC CCCAGGAAAA GCCACAGGCC TATCAGCCAG ACATGGTTAA       540

GGCAAATCAA GCAGAAAATG AGTCCACTCG ACAGTATGAA GGTCCACTGC ATCATTATCG       600

GTCCCAGCAG GAATCACCAT CTCCACAGCA ACAGCCACCA CTGCCCCCAT CTTCCCAGTC       660

AGAGGGAATG GGACAGGTGC CCAGGACCCA TCGACTGATC ACACTTGCTG ACCACATCTG       720

TCAAATTATC ACACAAGATT TTGCTAGAAA TCAAGTTCCC TCGCAGCCTT CTACTTCTAC       780

ATTCCAAACT TCACCATCTG CTTTGTCATC CACACCTGTA AGAACTAAAA CCTCAAGCCG       840

CTACAGCCCA GAATCACAGT CTCAGACTGT CTTGCATCCC AGACCAGGTC CTAGAGTCTC       900

TCCAGAAAAT CTTGTGGATA AATCCCGGGG AAGCAGGCCT GGAAAATCTC AGAGAGGAG       960

TCATATCCCA TCAGAGCCCT ATGAGCCCAT CTCCCCACCC CAAGGCCCTG CTGTGCATGA      1020

GAAGCAGGAC AGCATGTTGC TCTTGTCACA GAGGGGAGTG GACCCTGCTG AGCAAAGGAG      1080

TGATTCTCGA TCACCAGGAA GTATAAGCTA CTTGCCTTCA TTCTTCACCA AGCTTGAAAG      1140

CACATCACCC ATGGTTAAAT CAAAGAAACA GGAAATTTTT CGTAAGTTGA ACTCTTCTGG      1200

TGGAGGTGAC TCTGATATGG CAGCTGCTCA GCCAGGAACA GAGATCTTCA ATCTGCCAGC      1260

AGTTACCACA TCAGGTGCAG TGAGCTCAAG AAGCCATTCT TTTGCTGATC CCGCCAGTAA      1320

CCTTGGTCTA GAAGACATCA TCAGAAAGGC TCTCATGGGA AGTTTTGATG ATAAAGTTGA      1380

AGATCATGGT GTTGTCATGT CCCATCCTGT GGGCATTATG CCTGGTAGTG CCAGCACCTC      1440

AGTGGTGACG AGCAGCGAGG CACGGAGAGA TGAAGGGGAG CCATCACCTC ATGCAGGAGT      1500

ATGCAAACCA AAGCTGATCA ACAAATCAAA CAGCAGGAAG TCTAAATCTC CTATTCCTGG      1560

GCAAAGCTAT TTAGGAACTG AAAGGCCTTC TTCTGTCTCC TCTGTGCATT CAGAAGGTGA      1620

TTACCACAGG CAGACACCAG GATGGGCATG GAAGATCGG CCCTCTTCAA CAGGTTCTAC      1680

TCAGTTCCCT TACAACCCTC TGACCATACG GATGCTCAGC AGTACACCAC CTACACAGAT      1740

CGCATGCGCC CCATCTGCCA TCACCCAAGC AGCTCCACAT CAACAGAACC GCATCTGGGA      1800

GAGGGAGCCT GCCCCGCTCC TCTCAGCGCA GTATGAGACA CTGTCTGATA GTGACGACTG      1860
```

AGCTGTGCGT GGGAGAGCGC TCTGGCTTTG GTTTTTATTG AAGATTTAAA AAAAAAAAAA    1920

AA    1922

(2) INFORMATION FOR SEQ ID NO:10:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:10:

GURAGU    6

(2) INFORMATION FOR SEQ ID NO:11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GATCCGGGTA GGGTTCACCG AAAGTTCACT CGA    33

(2) INFORMATION FOR SEQ ID NO:12:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

CTAGACAAGG GTTCAATGCA CTTGTCCATC G    31

(2) INFORMATION FOR SEQ ID NO:13:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

AGGTCA    6

(2) INFORMATION FOR SEQ ID NO:14:

(i) SEQUENCE CHARACTERISTICS:
        (A) LENGTH: 1677 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

ATGCTAACAG AACACGCGGC AGGCCCTCTG GGGCAGAATC TGGATTTGGA ATCGTACTCC    60

```
CCATACAACA ATGTCCCGTT TCCTCAAGTT CAGCCACAGA TTTCCTCCTC GTCTTACTAT      120

TCCAACCTGG GCTTCTACCC CCAACAACCG GAAGACTGGT ATTCTCCTGG CATCTATGAA      180

CTCAGGCGAA TGCCCGCTGA GACTGGGTAC CAGGGAGAGA CTGAGGTATC AGAGATGCCT      240

GTGACAAAGA AGCCGCGAAT GGCCGCGGCA TCGGCAGGCA GAATAAAAGG GGATGAGCTG      300

TGTGTTGTCT GTGGAGACAG GGCCTCTGGG TACCACTACA ACGCGCTCAC CTGTGAGGGC      360

TGCAAAGGTT TCTTCCGAAG AAGCATTACC AAGAACGCCG TGTACAAGTG TAAGAACGGG      420

GGCAACTGCG TGATGGACAT GTACATGCGC AGGAAGTGCC AGGAGTGCCG GCTAAGGAAG      480

TGCAGAGAGA TGGGGATGTT GGCTGAATGT ATGTATACAG GTTTGTTAAC TGAAATCCAG      540

TGTAAATCTA AACGGCTAAG GAAAAATGTG AAGCAGCACG CTGATCAGAC AGTGAATGAG      600

GACGACAGCG AAGGGCGTGA CTTGCGACAA GTGACCTCCA CAACCAAGTT TTGCAGGGAG      660

AAAACGGAAC TCACGGCAGA CCAGCAGACC CTCCTGGATT ATATTATGGA TTCGTACAAC      720

AAACAGAGAA TGCCTCAGGA AATCACAAAT AAAATCTTAA AGAAGAATT TAGTGCAGAA       780

GAAAATTTTC TCATATTAAC AGAAATGGCA ACCAGCCATG TACAGATTCT CGTAGAATTC      840

ACAAAAAAGC TTCCAGGGTT TCAGACACTG GACCACGAAG ATCAGATTGC TTTGCTCAAA      900

GGGTCCGCAG TGGAGGCCAT GTTTCTTCGT TCGGCGGAGA TTTTCAATAA GAAACTTCCT      960

GCCGGACATG CAGACCTGTT GGAAGAAAGA ATTCGAAAGA GTGGTATCTC TGATGAGTAT     1020

ATAACCCCGA TGTTCAGTTT CTATAAAAGT GTTGGAGAAC TCAAAATGAC TCAGGAGGAG     1080

TACGCTCTGC TCACAGCGAT CGTCATCCTC TCTCCAGACA GACAATACAT CAAGGACAGA     1140

GAGGCGGTGG AGAAGCTGCA GGAGCCCCTG CTTGATGTGC TACAAAAGCT GTGCAAGATG     1200

TACCAGCCTG AGAACCCACA GCATTTCGCC TGCCTCCTGG GTCGCCTGAC GGAACTCCGG     1260

ACATTCAACC ATCACCACGC TGAGATGCTG ATGTCTTGGA GAGTGAATGA TCACAAGTTC     1320

ACCCCGCTCC TCTGTGAGAT CTGGGATGTG CAGTGATGGA CACCAGTGGG GCTGGCTCCT     1380

TGTCCTCCTC GGAACAGAAA CCTTGTTTCG TTTGTACCTG GTTTCACTCA AGAATCTCAA     1440

TGAATATTTA TGTGGCAATT ATACACCTCC CACGGTTGTA AATACAGACT AGATAGAACT     1500

GCTTTCCCCA CACTGTATTT TACAAGGCTT CAGGAAACCC CACTGGCATG CCCTTTTGGC     1560

CTAATTAAAT CAATTGTTAC TTCAATTCTA TCTACTGAGC TAGGGGCATA TTATTCTTCA     1620

TTCGACAATA TTATATATAT TTTATAAAGT TGAGCTGTTT TCAACTGAGA CAATAAA       1677

(2) INFORMATION FOR SEQ ID NO:15:

(i) SEQUENCE CHARACTERISTICS:
           (A) LENGTH: 60 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:15:

TGGTCACCCA GGCTTCTGCT TCAGTCTCTC CTCCTTCTCC TCCTCAGCCC ACTGTCTCCT       60

(2) INFORMATION FOR SEQ ID NO:16:

(i) SEQUENCE CHARACTERISTICS:
           (A) LENGTH: 60 base pairs
           (B) TYPE: nucleic acid
           (C) STRANDEDNESS: single
           (D) TOPOLOGY: linear
```

```
    (ii) MOLECULE TYPE: DNA (xi) SEQUENCE DESCRIPTION: SEQ ID NO:16:

AAAATTACTG GGCACTAGAA AGGAAGACTG GGCTCCGAAT CCTCTTAGAG CCTTGGACAT     60

(2) INFORMATION FOR SEQ ID NO:17:

(i) SEQUENCE CHARACTERISTICS:
        (A) LENGTH: 246 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

AGAGAAGAAC CGAGTTCTGA GAGTCTACAG CAAAATTACT GGGCACTAGA AAGGAAGACT     60

GGGCTCCGAA TCCTCTTAGA GCCTTGGACA TCTCTGGCCC AAAGCAATCC AAGGATCTTA    120

TTTGAGGACC ACCATCCCAG AAGTACTTTC TCAAGGTTGA AAAGTTGGAG TGGTAGCCAA    180

GATGAATCTG ATTGGGCACT CCATTTACAG GCTACGGACG AGTTTTCTCT TTCTGAAAGC    240

TTATTT                                                               246
```